(12) United States Patent
Mullen

(10) Patent No.: US 7,528,212 B2
(45) Date of Patent: May 5, 2009

(54) IONIZING RADIATION STABLE THERMOPLASTIC COMPOSITION, METHOD OF MAKING, AND ARTICLES FORMED THEREFROM

(75) Inventor: Brian Mullen, Mt. Vernon, IN (US)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 134 days.

(21) Appl. No.: 11/282,377

(22) Filed: Nov. 18, 2005

(65) Prior Publication Data

US 2007/0117957 A1 May 24, 2007

(51) Int. Cl.
C08G 63/00 (2006.01)
(52) U.S. Cl. .............. 528/190; 250/472.1; 250/474.1; 264/176.1; 264/219; 428/411.1; 428/412
(58) Field of Classification Search .............. 250/472.1, 250/474.1; 264/176.1, 219; 428/411.1, 412; 528/190
See application file for complete search history.

(56) References Cited

U.S. PATENT DOCUMENTS

| 4,026,913 | A | | 5/1977 | Tanigaichi et al. |
| 4,188,475 | A | | 2/1980 | Margotte |
| 4,880,850 | A | | 11/1989 | Nelson et al. |
| 4,933,424 | A | | 6/1990 | Rosenquist |
| 4,996,244 | A | | 2/1991 | Avakian |
| 4,996,248 | A | | 2/1991 | Nelson et al. ............... 523/136 |
| 5,118,726 | A | | 6/1992 | Mizutani et al. ............ 523/136 |
| 5,126,404 | A | * | 6/1992 | Eckel et al. ..................... 525/67 |
| 5,306,456 | A | * | 4/1994 | Suhadolnik et al. ..... 264/173.16 |
| 5,426,170 | A | * | 6/1995 | Hirao et al. .................. 528/198 |
| 5,807,908 | A | | 9/1998 | Hirose et al. ................ 523/136 |
| 6,040,367 | A | | 3/2000 | Miya et al. |
| 6,197,854 | B1 | | 3/2001 | Krishnan et al. ............ 524/111 |
| 6,297,300 | B1 | | 10/2001 | Van Nuffel ................... 524/91 |
| 6,359,028 | B1 | | 3/2002 | Miya et al. |
| 6,420,512 | B1 | | 7/2002 | McCloskey et al. |
| 6,870,025 | B2 | | 3/2005 | McCloskey et al. |
| 6,960,641 | B2 | | 11/2005 | O'Neil et al. |
| 2005/0113535 | A1 | | 5/2005 | Glasgow et al. |
| 2005/0288407 | A1 | | 12/2005 | Heuer et al. ............... 524/155 |
| 2006/0013849 | A1 | | 1/2006 | Strickler et al. ............ 424/422 |
| 2007/0100059 | A1 | | 5/2007 | Mullen |

FOREIGN PATENT DOCUMENTS

| EP | 0 152 012 A2 | 1/1985 |
| EP | 0 272 416 A2 | 11/1987 |
| EP | 0 272 417 A2 | 11/1987 |
| EP | 0 384 110 B1 | 1/1990 |
| EP | 0507547 A2 | 10/1992 |
| EP | 0525338 A1 | 2/1993 |
| EP | 0 640 646 A1 | 8/1994 |
| EP | 0 640 646 B1 | 8/1994 |
| EP | 1 221 459 A1 | 8/1994 |
| EP | 0 664 316 A1 | 1/1995 |
| EP | 0 753 540 A2 | 7/1996 |
| EP | 0 787 769 B1 | 1/1997 |
| EP | 0 794 218 A2 | 3/1997 |
| EP | 0 794 218 B1 | 3/1997 |
| EP | 0 970 996 B1 | 7/1998 |

OTHER PUBLICATIONS

JP63051429; Publication Date: Apr. 3, 1988 (translation of abstract only).
WO94/22938; Publication Date Oct. 13, 1994 (translation of abstract only).
Huang, S.J. et al "Polycarbonate Networks And Semi-Interpenetrating Networks From Biphenol-A-Polycarbonate Dicyanates", Polym. Prep. American Chemical Society Div. Polym. Chem. 1992, 33(1); pp. 950-951.
ASTM D 1925-70 (Reapproved 1988) "Standard Test Method for Yellowness Index of Plastics" pp. 1-3.
JP4328156. Publication Date: Nov. 17, 1992 "Polycarbonate Composition". (Abstract Only).

(Continued)

Primary Examiner—Terressa Boykin

(57) ABSTRACT

A thermoplastic composition comprises a polycarbonate that is not aryl carboxylate end-capped, and an aryl carboxylate end-capped polycarbonate of formula:

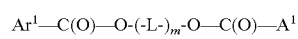

$$Ar^1—C(O)—O\text{-}(\text{-L-})_m\text{-}O—C(O)—A^1$$

wherein each $Ar^1$ is independently an aryl group, $\text{-}(\text{-L-})_m\text{-}$ is a polycarbonate linking group with m units of linking unit L, and m is at least one; wherein the aryl carboxylate end-capped polycarbonate has aryl carboxylate end groups present in the thermoplastic composition in an amount of 0.01 to 500 mmol/Kg based on the combined weights of the polycarbonate that is not aryl carboxylate end-capped, and the aryl carboxylate end-capped polycarbonate, and wherein a molded article having a thickness of 3.2±0.12 millimeters and consisting of the aryl carboxylate end-capped polycarbonate, the polycarbonate, and less than or equal to 1.0 percent total weight of aliphatic diol, a mold-release agent, and an antioxidant has, after exposure to a total gamma radiation dose of 81 kGy and when measured according to ASTM D1925-70, an increase in yellowness index (dYI) of less than or equal to 24.5, when compared to the unexposed molded article. A method for preparing the aryl carboxylate end-capped polycarbonate that is not aryl carboxylate end-capped, and thermoplastic composition, an article prepared from the thermoplastic composition, are also disclosed.

26 Claims, No Drawings

OTHER PUBLICATIONS

JP5239331. Publication Date: Sep. 17, 1993 "Production of Polycarbonate Resin Composition". (Abstract Only).
JP5239333. Publication date: Sep. 17, 1993. "Production of Polycarbonate Resin Composition". (Abstract Only).
JP5239332. Publication Date: Sep. 17, 1993. "Production of Polycarbonate Resin Composition and its Use". (Abstract Only).
JP7062077. Publication Date: Mar. 7, 1995. "Production of Polycarbonate Resin". (Abstract Only).
JP7126374. Publication Date: May 16, 1995. "Production of Polycarbonate Resin". (Abstract Only).
JP7165905. Publication Date: Jun. 27, 1995. "Production of Polycarboante Resin". (Abstract Only).
JP8059975. Publication Date: Mar. 5, 1996 "Production of Stabilized Polycarbonate". (Abstract Only).
JP9003314. Publication Date: Jan. 7, 1997 "Polycarbonate Resin Composition" (Abstract Only).
JP9025404. Publication Date: Jan. 28, 1997 "Polycarbonate Resin Composition". (Abstract Only).
JP9040854. Publication Date: Feb. 10, 1997 "Polycarbonate Resin Composition". (Abstract Only).
JP9087506. Publication Date: Mar. 31, 1997. "Polycarbonate Resin Composition". (Abstract Only).
JP9143354. Publication Date: Jun. 3, 1997. "Polycarbonate Resin Composition". (Abstract Only).
JP9143355. Publication Date: Jun. 3, 1997. "Polycarbonate Resin Composition". (Abstract Only).
JP9227771. Publication Date: Sep. 2, 1997. "Polycarbonate Resin Composition". (Abstract Only).
JP9241497. Publication Date: Sep. 16, 1997. "Polycarbonate Resin Composition". (Abstract Only).
JP9249804. Publication Date: Sep. 22, 1997. "Polycarbonate Resin Composition". (Abstract Only).
JP9255862. Publication Date: Sep. 30, 1997. "Polycarbonate Resin Composition". (Abstract Only).
JP9279007. Publication Date: Oct. 28, 1997. "Polycarbonate Resin Composition". (Abstract Only).
JP9279008. Publication Date: Oct. 28, 1997. "Polycarbonate Resin Composition". (Abstract Only).
JP9302208. Publication Date: Nov. 25, 1997. "Polycarbonate Resin Composition". (Abstract Only).
JP11100497. Publication Date: Apr. 13, 1999. "Aromatic Polycarbonate Composition". (Abstract Only).
JP2000226505. Publication Date: Aug. 15, 2000. "Polycarbonate Resin Composition" (Abstract Only).
JP2000239511. Publication Date: Sep. 5, 2000. "Stabilized Aromatic Polycarbonate Composition and Injection Molded Product Therefrom". (Abstract Only).
JP197864262. Publication Date: Aug. 6, 1978. "Method of Stabilizing Polycarbonate Resin" (Abstract Only).
JP63213550A2. Publication Date: Sep. 6, 1988. "Blend of Copolyester Carbonate Resin and Polyester Resin Showing Improved Color Characteristic". (Abstract Only).
JP63213554A2. Publication Date: Sep. 6, 1988. "Blend of Polycarbonate Resin and Polyester Resin Showing Improved Color Characteristics". (Abstract Only).
Tachikawa, et al. "Development of Polymer Films Containing Tris-(sulfonyloxy)benzene Analogs for Y Rays Detection", Journal of Photopolymer Science and Technology. vol. 17, No. 1 (2004). pp. 81-86.
International Search Report; International Application No. PCT/US2006/044072; Date of Mailing: May 22, 2007.
Written Opinion; International Application No. PCT/US2006/044072; Date of Mailing: May 22, 2007.
International Search Report for International Application No. PCT/US2006/042183, mailed Mar. 29, 2007, 3 pages.
Japanese Patent Publication No. 63051429, published Mar. 4, 1988, Abstract Only, 1 page.

* cited by examiner

IONIZING RADIATION STABLE THERMOPLASTIC COMPOSITION, METHOD OF MAKING, AND ARTICLES FORMED THEREFROM

BACKGROUND OF THE INVENTION

This disclosure relates to stabilized thermoplastic compositions, methods of manufacture, and articles and uses thereof.

Irradiation using electron beam (e-beam) radiation or gamma ray (γ-ray) radiation (also referred to as "gamma radiation") is increasingly used to sterilize lightweight or disposable plastic articles for use in hospitals, biological laboratories, manufacturers of medical devices, and other end-users of sterile equipment. Gamma ray sources such as, for example, $^{60}$Co, which emits a β-particle and gamma ray radiation at 1.17 and 1.33 megaelectron volts (MeV), can be used for sterilization. Some advantages of gamma ray radiation are that it is more penetrating than E-beam radiation, leaves no residue, and can be less damaging to plastics than heat and/or moisture. Because of the ability of gamma rays to penetrate plastics, articles that have already been packaged and/or assembled may conveniently be sterilized. Further, use of such radiation is ideal for sterilizing large numbers of articles, such as those made from plastics, due to the penetrating ability of gamma radiation, wherein the units closer to the source can receive a similar dose to those furthest from the source. Articles such as blood bags, petri dishes, syringes, beakers, vials, centrifuge tubes, spatulas, and the like, as well as prepackaged articles, are desirably sterilized using this method.

Thermoplastics are useful for preparing articles such as those listed above. In particular, polycarbonates, with their balance of properties including transparency, low color, impact resistance, ductility, and melt flow, are desirable for use as materials of construction. However, exposure of polycarbonates to gamma ray doses suitable for sterilization (typically nominal doses of 10 to 85 kiloGrays (kGy), wherein 1 Gray equals 1 Joule of absorbed energy per kilogram of mass) can result in observable yellowing of the polycarbonate, and may further result in the degradation of one or more mechanical properties. Stabilizers, also referred to in the art as "anti-rads", may be used to mitigate the effects of the gamma ray dose on plastics generally. Stabilizers present in amounts sufficient to reduce yellowing in thermoplastic compositions comprising polycarbonates may also affect one or more of the desirable mechanical properties of the thermoplastic composition, such as, for example, impact strength and/or ductility. The usefulness of stabilizers to reduce yellowing in thermoplastic compositions of polycarbonate upon gamma ray exposure can, in this way, be mitigated by these secondary considerations of mechanical properties.

There accordingly remains a need in the art for improved stabilizers for polycarbonate compositions, as well as polycarbonate compositions having improved resistance to gamma ray radiation.

SUMMARY OF THE INVENTION

The above deficiencies in the art are alleviated by, in an embodiment, a thermoplastic composition comprising a polycarbonate that is not aryl carboxylate end-capped, and an aryl carboxylate end-capped polycarbonate of formula:

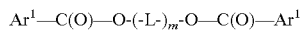

wherein each $Ar^1$ is independently an aryl group, wherein $-(-L-)_m-$ is a polycarbonate linking group with m units of linking unit L, and wherein m is at least one; wherein the aryl carboxylate end-capped polycarbonate has aryl carboxylate end groups present in the thermoplastic composition in an amount of 0.01 to 500 mmol/Kg based on the combined weights of the polycarbonate that is not aryl carboxylate end-capped, and the aryl carboxylate end-capped polycarbonate, and wherein a molded article having a thickness of 3.2±0.12 millimeters and consisting of the aryl carboxylate end-capped polycarbonate, the polycarbonate, and less than or equal to 1.0 percent total weight of aliphatic diol, a mold-release agent, and an antioxidant has, after exposure to a total gamma radiation dose of 81 kGy and when measured according to ASTM D1925-70, an increase in yellowness index (dYI) of less than or equal to 24.5, when compared to the unexposed molded article.

In another embodiment, a thermoplastic composition comprises a polycarbonate that is not aryl carboxylate end-capped, and an aryl carboxylate end-capped polycarbonate of formula:

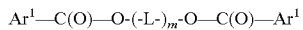

wherein each $Ar^1$ is independently an aryl group, and $-(-L-)_m-$ is a polycarbonate linking group with m units of linking unit L, wherein m is at least one; and wherein the aryl carboxylate end-capped polycarbonate has aryl carboxylate end groups present in amount of 0.01 to 10 mole-percent based on the total number of moles of linking unit L present in the aryl carboxylate end-capped polycarbonate; and wherein the aryl carboxylate end-capped polycarbonate is present in an amount of 0.1 to 100 wt %, based on the total weight of the polycarbonate that is not aryl carboxylate end-capped, and aryl carboxylate end-capped polycarbonate, with the proviso that the amount and type of aryl carboxylate end-capped polycarbonate used is selected so that the overall concentration of aryl carboxylate end groups is less than or equal to a molar concentration of 500 millimoles per kilogram (mmol/Kg), and is greater than or equal to 0.01 mmol/Kg, of the total weight of the polycarbonate that is not aryl carboxylate end-capped, and aryl carboxylate end-capped polycarbonate.

In another embodiment, a method of preparing an aryl carboxylate end-capped polycarbonate comprises condensing: a dihydroxy compound, an aryl carboxylic acid halide, and an activated carbonyl compound in a biphasic medium at a pH of about 9 to about 11, wherein the activated carbonyl compound is phosgene, diphosgene, triphosgene, a dichloroformate, or a combination comprising at least one of these, and wherein the aryl carboxylate end-capped polycarbonate has aryl carboxylate end groups present in an amount of 0.01 to 10 mole-percent based on the total number of moles of linking unit L present in the aryl carboxylate end-capped polycarbonate.

In another embodiment, a method of making a thermoplastic composition comprises melt-blending: a polycarbonate that is not aryl carboxylate end-capped, and an aryl carboxylate end-capped polycarbonate of formula:

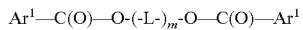

wherein each $Ar^1$ is independently an aryl group, and $-(-L-)_m-$ is a polycarbonate linking group with m units of linking unit L, wherein m is at least one; wherein the aryl carboxylate end-capped polycarbonate has aryl carboxylate end groups present in amount of 0.01 to 10 mole-percent based on the total number of moles of linking unit L present in the aryl carboxylate end-capped polycarbonate, and wherein the aryl carboxylate end-capped polycarbonate is present in an amount of 0.1 to 100 wt %, based on the total weight of the polycarbonate that is not aryl carboxylate end-capped, and aryl carboxylate end-capped polycarbonate, with the proviso that the amount and type of aryl carboxylate end-capped polycarbonate used is selected so that the overall concentration of aryl carboxylate end groups is less than or equal to a molar concentration of 500 millimoles per kilogram (mmol/Kg), and is greater than or equal to 0.01 mmol/Kg, of the total weight of the polycarbonate that is not aryl carboxylate end-capped, and aryl carboxylate end-capped polycarbonate.

A sterilization method comprising exposing an article to radiation wherein the article comprises a polycarbonate that is not aryl carboxylate end-capped, and an aryl carboxylate end-capped polycarbonate of formula:

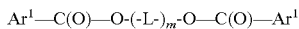

$$Ar^1\text{—}C(O)\text{—}O\text{-}(\text{-}L\text{-})_m\text{-}O\text{—}C(O)\text{—}Ar^1$$

wherein each $Ar^1$ is independently an aryl group, $-(\text{-}L\text{-})_m$- is a polycarbonate linking group with m units of linking unit L, and m is at least one; wherein the aryl carboxylate end-capped polycarbonate has aryl carboxylate end groups present in the thermoplastic composition in an amount of 0.01 to 500 mmol/Kg based on the combined weights of the polycarbonate that is not aryl carboxylate end-capped, and the aryl carboxylate end-capped polycarbonate.

In another embodiment, a thermoplastic composition consists essentially of a polycarbonate that is not aryl carboxylate end-capped, and an aryl carboxylate end-capped polycarbonate of formula:

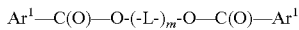

$$Ar^1\text{—}C(O)\text{—}O\text{-}(\text{-}L\text{-})_m\text{-}O\text{—}C(O)\text{—}Ar^1$$

wherein each $Ar^1$ is independently an aryl group, $-(\text{-}L\text{-})_m$- is a polycarbonate linking group with m units of linking unit L, and m is at least one; wherein the aryl carboxylate end-capped polycarbonate has aryl carboxylate end groups present in the thermoplastic composition in an amount of 0.01 to 500 mmol/Kg based on the combined weights of the polycarbonate that is not aryl carboxylate end-capped, and the aryl carboxylate end-capped polycarbonate, and wherein a molded article having a thickness of 3.2±0.12 millimeters and consisting of the aryl carboxylate end-capped polycarbonate, the polycarbonate that is not aryl carboxylate end-capped, and less than or equal to 1.0 percent total weight of aliphatic diol, a mold-release agent, and an antioxidant has, after exposure to a total gamma radiation dose of 81 kGy and when measured according to ASTM D1925-70, an increase in yellowness index (dYI) of less than or equal to 24.5, when compared to the unexposed molded article.

In another embodiment, an article comprising the thermoplastic composition is disclosed.

The above described and other features are exemplified by the following detailed description.

DETAILED DESCRIPTION OF THE INVENTION

Surprisingly, it has been found that a thermoplastic composition comprising a polycarbonate that is not aryl carboxylate end-capped, and a specific type of aryl carboxylate end-capped polycarbonate has significantly improved resistance to yellowing upon exposure to gamma radiation. The use of the aryl carboxylate end-capped polycarbonate helps maintain the mechanical properties at the same or comparable level as an unstabilized thermoplastic composition comprising polycarbonate that is not aryl carboxylate end-capped.

As used herein, the term "alkyl" refers to a straight or branched chain monovalent hydrocarbon group; "alkylene" refers to a straight or branched chain divalent hydrocarbon group; "alkylidene" refers to a straight or branched chain divalent hydrocarbon group, with both valences on a single common carbon atom; "alkenyl" refers to a straight or branched chain monovalent hydrocarbon group having at least two carbons joined by a carbon-carbon double bond; "cycloalkyl" refers to a non-aromatic monovalent monocyclic or multicyclic hydrocarbon group having at least three carbon atoms, "cycloalkylene" refers to a non-aromatic alicyclic divalent hydrocarbon group having at least three carbon atoms, with at least one degree of unsaturation; "aryl" refers to an aromatic monovalent group containing only carbon in the aromatic ring or rings; "arylene" refers to an aromatic divalent group containing only carbon in the aromatic ring or rings; "alkylaryl" refers to an aryl group that has been substituted with an alkyl group as defined above, with 4-methylphenyl being an exemplary alkylaryl group; "arylalkyl" refers to an alkyl group that has been substituted with an aryl group as defined above, with benzyl being an exemplary arylalkyl group; "acyl" refers to a an alkyl group as defined above with the indicated number of carbon atoms attached through a carbonyl carbon bridge (—C(=O)—); "alkoxy" refers to an alkyl group as defined above with the indicated number of carbon atoms attached through an oxygen bridge (—O—); and "aryloxy" refers to an aryl group as defined above with the indicated number of carbon atoms attached through an oxygen bridge (—O—).

Unless otherwise indicated, each of the foregoing groups may be unsubstituted or substituted, provided that the substitution does not significantly adversely affect synthesis, stability, or use of the compound. The term "substituted" as used herein means that any one or more hydrogens on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound.

The thermoplastic composition comprises a polycarbonate. As used herein, the terms "polycarbonate" and "polycarbonate resin" means compositions having repeating structural carbonate units of the formula (1):

(1)

in which at least 60 percent of the total number of $R^1$ groups are aromatic organic radicals and the balance thereof are aliphatic, alicyclic, or aromatic radicals. In one embodiment, each $R^1$ is an aromatic organic radical. In another embodiment, each $R^1$ is a radical of the formula (2):

$$\text{-}A^1\text{-}Y^1\text{-}A^2\text{-}$$ (2)

wherein each of $A^1$ and $A^2$ is a monocyclic divalent aryl radical and $Y^1$ is a bridging radical having one or two atoms that separate $A^1$ from $A^2$. In an exemplary embodiment, one atom separates $A^1$ from $A^2$. Illustrative non-limiting examples of radicals of this type are —O—, —S—, —S(O)—, —S(O$_2$)—, —C(O)—, methylene, cyclohexyl-methylene, 2-[2.2.1]-bicycloheptylidene, ethylidene, isopropylidene, neopentylidene, cyclohexylidene, cyclopentadecylidene, cyclododecylidene, and adamantylidene. The bridging radical $Y^1$ may be a hydrocarbon group or a saturated hydrocarbon group such as methylene, cyclohexylidene, or isopropylidene. In another embodiment, $Y^1$ is a carbon-carbon bond (—) connecting $A^1$ and $A^2$.

Polycarbonates may be produced by the interfacial reaction of dihydroxy compounds having the formula HO—$R^1$—OH, which includes dihydroxy aromatic compounds of formula (3):

wherein $Y^1$, $A^1$ and $A^2$ are as described above. Also included are bisphenol compounds of general formula (4):

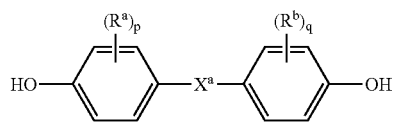

wherein $R^a$ and $R^b$ each represent a halogen atom or a monovalent hydrocarbon group and may be the same or different; p and q are each independently integers of 0 to 4; and $X^a$ represents one of the groups of formula (5):

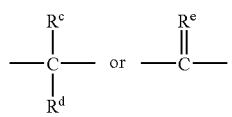

wherein $R^c$ and $R^d$ each independently represent a hydrogen atom or a monovalent linear alkyl or cyclic alkylene group and $R^e$ is a divalent hydrocarbon group. In an embodiment, $R^c$ and $R^d$ represent a cyclic alkylene group comprising carbon atoms, heteroatoms with a valency of two or greater, or a combination comprising at least one heteroatom and at least two carbon atoms. Suitable heteroatoms include —O—, —S—, and —N(Z)-, where $Ar^1$ is a substituent group selected from hydrogen, halogen, hydroxy, $C_{1-12}$ alkyl, $C_{1-12}$ alkoxy, or $C_{1-12}$ acyl. Where present, the cyclic alkylene group may have 3 to 20 carbons, and may be a single saturated or unsaturated ring, or fused polycyclic ring system wherein the fused rings are saturated, unsaturated, or aromatic.

Suitable polycarbonates further include those derived from bisphenols containing alkyl cyclohexane units. Such polycarbonates have structural units corresponding to the formula (6):

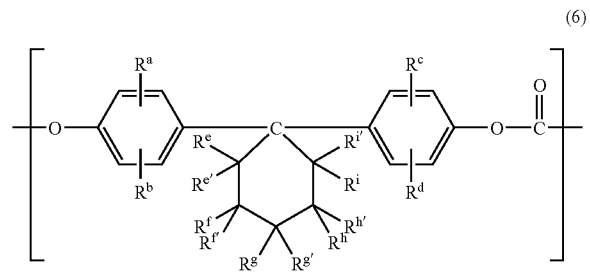

wherein $R^a$—$R^d$ are each independently hydrogen, $C_{1-12}$ alkyl, or halogen; and substituents $R_e$—$R_i$ and $R_{e'}$—$R_{i'}$ are each independently hydrogen or $C_{1-12}$ alkyl. The substituents may be aliphatic or aromatic, straight-chain, cyclic, bicyclic, branched, saturated, or unsaturated. In a specific embodiment, alkyl cyclohexane-containing bisphenols, for example the reaction product of two moles of a phenol with one mole of a hydrogenated isophorone, are useful for making polycarbonate polymers with high glass transition temperatures and high heat distortion temperatures. Such isophorone bisphenol-containing polycarbonates correspond to formula (6), wherein each of $R_f$, $R_{f'}$, and $R_h$ are methyl groups; $R_e$, $R_{e'}$, $R_g$, $R_{g'}$, $R_{h'}$, $R_i$, and $R_{i'}$ are each hydrogen; and $R_a$—$R_d$ are as defined above. These isophorone bisphenol based polymers, including polycarbonate copolymers made containing non-alkyl cyclohexane bisphenols and blends of alkyl cyclohexyl bisphenol containing polycarbonates with non-alkyl cyclohexyl bisphenol polycarbonates, are supplied by Bayer Co. under the APEC® trade name.

Some illustrative, non-limiting examples of suitable dihydroxy compounds include the following: 4,4'-dihydroxybiphenyl, 1,6-dihydroxynaphthalene, 2,6-dihydroxynaphthalene, bis(4-hydroxyphenyl)methane, bis(4-hydroxyphenyl) diphenylmethane, bis(4-hydroxyphenyl)-1-naphthylmethane, 1,2-bis(4-hydroxyphenyl)ethane, 1,1-bis (4-hydroxyphenyl)-1-phenylethane, 2-(4-hydroxyphenyl)-2-(3-hydroxyphenyl)propane, bis(4-hydroxyphenyl) phenylmethane, 2,2-bis(4-hydroxy-3-bromophenyl) propane, 1,1-bis (hydroxyphenyl)cyclopentane, 1,1-bis(4-hydroxyphenyl)cyclohexane, 1,1-bis(4-hydroxy-3 methyl phenyl)cyclohexane 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantine, (alpha, alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl) propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl) propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis (4-hydroxyphenyl)sulfone, 9,9-bis(4-hydroxyphenyl) fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, and the like, as well as combinations comprising at least one of the foregoing dihydroxy compounds.

Specific examples of the types of bisphenol compounds represented by formula (3) include 1,1-bis(4-hydroxyphenyl) methane, 1,1-bis(4-hydroxyphenyl) ethane, 2,2-bis(4-hydroxyphenyl) propane (hereinafter "bisphenol A" or "BPA"), 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-1-methylphenyl) propane, 1,1-bis(4-hydroxy-t-butylphenyl) propane, 3,3-bis (4-hydroxyphenyl)phthalimidine, 2-phenyl-3,3-bis(4-hydroxyphenyl)phthalimidine (PPPBP), and 1,1-bis(4-hydroxy-3-methylphenyl)cyclohexane (DMBPC). Combinations comprising at least one of the foregoing dihydroxy compounds may also be used.

Another dihydroxy aromatic group $R^1$ is derived from a dihydroxy aromatic compound of formula (7):

(7)

wherein each $R^f$ is independently a halogen atom, a $C_{1-10}$ hydrocarbon group, or a $C_{1-10}$ halogen substituted hydrocarbon group, and n is 0 to 4. The halogen is usually bromine. Examples of compounds that may be represented by the formula (7) include resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like; or combinations comprising at least one of the foregoing compounds.

In a specific embodiment, the polycarbonate is a linear homopolymer derived from bisphenol A, in which each of $A^1$ and $A^2$ is p-phenylene and $Y^1$ is isopropylidene. The polycarbonates may have an intrinsic viscosity, as determined in chloroform at 25° C., of 0.3 to 1.5 deciliters per gram (dl/g), specifically 0.45 to 1.0 dl/g. The polycarbonates may have a weight average molecular weight (Mw) of 10,000 to 100,000, as measured by gel permeation chromatography (GPC) using a crosslinked styrene-divinyl benzene column, at a sample concentration of 1 milligram per milliliter, and as calibrated with polycarbonate standards.

In an embodiment, the polycarbonate has flow properties suitable for the manufacture of thin articles. Melt volume flow rate (often abbreviated MVR) measures the rate of extrusion of a thermoplastics through an orifice at a prescribed temperature and load. Polycarbonates suitable for the formation of thin articles may have an MVR, measured at 300° C./1.2 kg according to ASTM D1238-04, of 0.5 to 80 cubic centimeters per 10 minutes (cc/10 min). In a specific embodiment, a suitable polycarbonate composition has an MVR measured at 300° C./1.2 kg according to ASTM D1238-04, of 0.5 to 100 cc/10 min, specifically 0.5 to 75 cc/10 min, and more specifically 1 to 50 cc/10 min. Mixtures of polycarbonates of different flow properties may be used to achieve the overall desired flow property.

The polycarbonate may have a light transmittance greater than or equal to 55%, specifically greater than or equal to 60% and more specifically greater than or equal to 70%, as measured at 3.2±0.12 millimeters thickness according to ASTM D1003-00. The polycarbonate may also have a haze less than or equal to 50%, specifically less than or equal to 40%, and most specifically less than or equal to 30%, as measured at 3.2±0.12 millimeters thickness according to ASTM D1003-00.

"Polycarbonates" and "polycarbonate resins" as used herein further include homopolycarbonates, copolymers comprising different $R^1$ moieties in the carbonate (referred to herein as "copolycarbonates"), copolymers comprising carbonate units and other types of polymer units, such as ester units, and combinations comprising one or more of homopolycarbonates and copolycarbonates. As used herein, "combination" is inclusive of blends, mixtures, alloys, reaction products, and the like. A specific type of copolymer is a polyester carbonate, also known as a polyester-polycarbonate. Such copolymers further contain, in addition to recurring carbonate chain units of the formula (1), repeating units of formula (8):

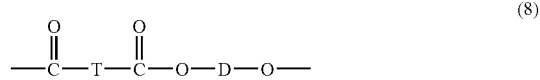

(8)

wherein D is a divalent radical derived from a dihydroxy compound, and may be, for example, a $C_{2-10}$ alkylene radical, a $C_{6-20}$ alicyclic radical, a $C_{6-20}$ aromatic radical or a polyoxyalkylene radical in which the alkylene groups contain 2 to 6 carbon atoms, specifically 2, 3, or 4 carbon atoms; and T divalent radical derived from a dicarboxylic acid, and may be, for example, a $C_{2-10}$ alkylene radical, a $C_{6-20}$ alicyclic radical, a $C_{6-20}$ alkyl aromatic radical, or a $C_{6-20}$ aromatic radical.

In one embodiment, D is a $C_{2-6}$ alkylene radical. In another embodiment, D is derived from an aromatic dihydroxy compound of formula (4) above. In another embodiment, D is derived from an aromatic dihydroxy compound of formula (7) above.

Examples of aromatic dicarboxylic acids that may be used to prepare the polyesters include isophthalic or terephthalic acid, 1,2-di(p-carboxyphenyl)ethane, 4,4'-dicarboxydiphenyl ether, 4,4'-bisbenzoic acid, and mixtures comprising at least one of the foregoing acids. Acids containing fused rings can also be present, such as in 1,4-, 1,5-, or 2,6-naphthalenedicarboxylic acids. Specific dicarboxylic acids are terephthalic acid, isophthalic acid, naphthalene dicarboxylic acid, cyclohexane dicarboxylic acid, or mixtures thereof. A specific dicarboxylic acid comprises a mixture of isophthalic acid and terephthalic acid wherein the weight ratio of terephthalic acid to isophthalic acid is 91:1 to 2:98. In another specific embodiment, D is a $C_{2-6}$ alkylene radical and T is p-phenylene, m-phenylene, naphthalene, a divalent cycloaliphatic radical, or a mixture thereof. This class of polyester includes the poly(alkylene terephthalates).

In addition to the ester units, the polyester-polycarbonates comprise carbonate units as described hereinabove. Carbonate units of formula (1) may also be derived from aromatic dihydroxy compounds of formula (7), wherein specific carbonate units are resorcinol carbonate units.

Specifically, the polyester unit of a polyester-polycarbonate can be derived from the reaction of a combination of isophthalic and terephthalic diacids (or derivatives thereof) with resorcinol, bisphenol A, or a combination comprising at least one of these, wherein the molar ratio of isophthalate units to terephthalate units is 91:9 to 2:98, specifically 85:15 to 3:97, more specifically 80:20 to 5:95, and still more specifically 70:30 to 10:90. The polycarbonate units can be derived from resorcinol and/or bisphenol A, in a molar ratio of resorcinol carbonate units to bisphenol A carbonate units of 0:100 to 99:1, and the molar ratio of the mixed isophthalate-terephthalate polyester units to the polycarbonate units in the polyester-polycarbonate can be 1:99 to 99:1, specifically 5:95 to 90:10, more specifically 10:90 to 80:20. Where a blend of polyester-polycarbonate with polycarbonate is used, the ratio of polycarbonate to polyester-polycarbonate in the blend can be, respectively, 1:99 to 99:1, specifically 10:90 to 90:10.

The polyester-polycarbonates may have a weight-averaged molecular weight (Mw) of 1,500 to 100,000, specifically 1,700 to 50,000, and more specifically 2,000 to 40,000. Molecular weight determinations are performed using gel permeation chromatography (GPC), using a crosslinked styrene-divinylbenzene column and calibrated to polycarbonate references. Samples are prepared at a concentration of about 1 mg/ml, and are eluted at a flow rate of about 1.0 ml/min.

Suitable polycarbonates can be manufactured by processes such as interfacial polymerization and melt polymerization. Although the reaction conditions for interfacial polymerization may vary, an exemplary process generally involves dissolving or dispersing a dihydric phenol reactant in aqueous caustic soda or potash, adding the resulting mixture to a suitable water-immiscible solvent medium, and contacting the reactants with a carbonate precursor in the presence of a suitable catalyst such as triethylamine or a phase transfer catalyst, under controlled pH conditions, e.g., 8 to 10. The most commonly used water immiscible solvents include methylene chloride, 1,2-dichloroethane, chlorobenzene, toluene, and the like. Suitable carbonate precursors include, for example, a carbonyl halide such as carbonyl bromide or carbonyl chloride, or a haloformate such as a bishaloformates of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors may also be used. A chain stopper (also referred to as a capping agent) may be included during polymerization. The chain-stopper limits molecular weight growth rate, and so controls molecular weight in the polycarbonate. A chain-stopper may be at least one of mono-phenolic compounds, mono-carboxylic acid chlorides, and/or mono-chloroformates. Where a chain stopper is incorporated with the polycarbonate, the chain stopper may also be referred to as an end group.

For example, mono-phenolic compounds suitable as chain stoppers include monocyclic phenols, such as phenol, $C_1$-$C_{22}$ alkyl-substituted phenols, p-cumyl-phenol, p-tertiary-butyl phenol, hydroxy diphenyl; monoethers of diphenols, such as p-methoxyphenol. Alkyl-substituted phenols include those with branched chain alkyl substituents having 8 to 9 carbon atoms. A mono-phenolic UV absorber may be used as capping agent. Such compounds include 4-substituted-2-hydroxybenzophenones and their derivatives, aryl salicylates, monoesters of diphenols such as resorcinol monobenzoate, 2-(2-hydroxyaryl)-benzotriazoles and their derivatives, 2-(2-hydroxyaryl)-1,3,5-triazines and their derivatives, and the like. Specifically, mono-phenolic chain-stoppers include phenol, p-cumylphenol, and/or resorcinol monobenzoate.

Mono-carboxylic acid chlorides may also be suitable as chain stoppers. These include monocyclic, mono-carboxylic acid chlorides such as benzoyl chloride, $C_1$-$C_{22}$ alkyl-substituted benzoyl chloride, 4-methylbenzoyl chloride, halogen-substituted benzoyl chloride, bromobenzoyl chloride, cinnamoyl chloride, 4-nadimidobenzoyl chloride, and mixtures thereof; polycyclic, mono-carboxylic acid chlorides such as trimellitic anhydride chloride, and naphthoyl chloride; and mixtures of monocyclic and polycyclic mono-carboxylic acid chlorides. Chlorides of aliphatic monocarboxylic acids with up to 22 carbon atoms are suitable. Functionalized chlorides of aliphatic monocarboxylic acids, such as acryloyl chloride and methacryoyl chloride, are also suitable. Also suitable are mono-chloroformates including monocyclic, mono-chloroformates, such as phenyl chloroformate, alkyl-substituted phenyl chloroformate, p-cumyl phenyl chloroformate, toluene chloroformate, and mixtures thereof.

Among the phase transfer catalysts that may be used in interfacial polymerization are catalysts of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Suitable phase transfer catalysts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, and $CH_3[CH_3(CH_2)_2]_3NX$, wherein X is Cl$^-$, Br$^-$, a $C_{1-8}$ alkoxy group or a $C_{6-18}$ aryloxy group. In an embodiment, a specifically useful phase transfer catalyst is $CH_3[CH_3(CH_2)_3]_3NCl$ (methyl tri-n-butyl ammonium chloride). An effective amount of a phase transfer catalyst may be 0.1 to 10 wt % based on the weight of bisphenol in the phosgenation mixture. In another embodiment an effective amount of phase transfer catalyst may be 0.5 to 2 wt % based on the weight of dihydroxy compound in the phosgenation mixture.

Alternatively, melt processes may be used to make the polycarbonates. Generally, in the melt polymerization process, polycarbonates may be prepared by co-reacting, in a molten state, the dihydroxy reactant(s) and a diaryl carbonate ester, such as diphenyl carbonate, in the presence of a transesterification catalyst in a Banbury® mixer, twin screw extruder, or the like to form a uniform dispersion. Volatile monohydric phenol is removed from the molten reactants by distillation and the polymer is isolated as a molten residue. A specifically useful melt process for making polycarbonates uses, a diaryl carbonate ester having electron withdrawing substituents on the aryls. Examples of specifically useful diaryl carbonate esters with electron withdrawing substituents include bis(4-nitrophenyl)carbonate, bis(2-chlorophenyl)carbonate, bis(4-chlorophenyl)carbonate, bis(methyl salicyl)carbonate, bis(4-methylcarboxylphenyl) carbonate, bis(2-acetylphenyl) carboxylate, bis(4-acetylphenyl) carboxylate, or a combination comprising at least one of these. In addition, suitable transesterification catalyst for use may include phase transfer catalysts of formula $(R^3)_4Q^+X$ above, wherein each $R^3$, Q, and X are as defined above. Examples of suitable transesterification catalysts include tetrabutylammonium hydroxide, methyltributylammonium hydroxide, tetrabutylammonium acetate, tetrabutylphosphonium hydroxide, tetrabutylphosphonium acetate, tetrabutylphosphonium phenolate, or a combination comprising at least one of these.

Branched polycarbonates are also useful, as well as blends of a linear polycarbonate and a branched polycarbonate. The branched polycarbonates may be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl) alpha, alpha-dimethyl benzyl)phenol), 4-chloroformyl phthalic anhydride, trimesic acid, and benzophenone tetracarboxylic acid. The branching agents may be added at a level of 0.05 to 2.0 wt % of the polycarbonate. All types of polycarbonate end groups are contemplated as being useful in the polycarbonate, provided that such end groups do not significantly affect desired properties of the thermoplastic compositions.

The polyester-polycarbonates may also be prepared by interfacial polymerization. Rather than utilizing the dicarboxylic acid per se, it is possible, and sometimes even preferred, to employ the reactive derivatives of the acid, such as the corresponding dicarboxylic acid dihalides, in particular the dicarboxylic acid dichlorides and the dicarboxylic acid dibromides. Thus, for example instead of using isophthalic acid, terephthalic acid, or mixtures thereof, it is possible to employ isophthaloyl dichloride, terephthaloyl dichloride, and mixtures thereof.

In addition to the polycarbonates described above, combinations of the polycarbonate with other thermoplastic polymers, for example combinations of homopolycarbonates and/or polycarbonate copolymers with polyesters, may be used. Suitable polyesters may include, for example, polyesters having repeating units of formula (8), which include poly(alkylene dicarboxylates), liquid crystalline polyesters, and polyester copolymers. The polyesters described herein are generally completely miscible with the polycarbonates when blended.

The polyesters may be obtained by interfacial polymerization or melt-process condensation as described above, by solution phase condensation, or by transesterification polymerization wherein, for example, a dialkyl ester such as dimethyl terephthalate may be transesterified with ethylene glycol using acid catalysis, to generate poly(ethylene terephthalate). It is possible to use a branched polyester in which a branching agent, for example, a glycol having three or more hydroxyl groups or a trifunctional or multifunctional carboxylic acid has been incorporated. Furthermore, it is sometime desirable to have various concentrations of acid and hydroxyl end groups on the polyester, depending on the ultimate end use of the composition.

Useful polyesters may include aromatic polyesters, poly (alkylene esters) including poly(alkylene arylates), and poly (cycloalkylene diesters). Aromatic polyesters may have a polyester structure according to formula (8), wherein D and T are each aromatic groups as described hereinabove. In an embodiment, useful aromatic polyesters may include, for example, poly(isophthalate-terephthalate-resorcinol) esters, poly(isophthalate-terephthalate-bisphenol-A) esters, poly [(isophthalate-terephthalate-resorcinol) ester-co-(isophthalate-terephthalate-bisphenol-A)] ester, or a combination comprising at least one of these. Also contemplated are aromatic polyesters with a minor amount, e.g., from about 0.5 to about 10 percent by weight, of units derived from an aliphatic diacid and/or an aliphatic polyol to make copolyesters.

Poly(alkylene arylates) may have a polyester structure according to formula (8), wherein T comprises groups derived from aromatic dicarboxylates, cycloaliphatic dicarboxylic acids, or derivatives thereof. Examples of specifically useful T groups include 1,2-, 1,3-, and 1,4-phenylene; 1,4- and 1,5- naphthylenes; cis- or trans-1,4-cyclohexylene; and the like. Specifically, where T is 1,4-phenylene, the poly (alkylene arylate) is a poly(alkylene terephthalate). In addition, for poly(alkylene arylate), specifically useful alkylene groups D include, for example, ethylene, 1,4-butylene, and bis-(alkylene-disubstituted cyclohexane) including cis- and/or trans-1,4-(cyclohexylene)dimethylene.

Examples of poly(alkylene terephthalates) include poly (ethylene terephthalate) (PET), poly(1,4-butylene terephthalate) (PBT), and poly(propylene terephthalate) (PPT). Also useful are poly(alkylene naphthoates), such as poly(ethylene naphthanoate) (PEN), and poly(butylene naphthanoate) (PBN). A specifically suitable poly(cycloalkylene diester) is poly(cyclohexanedimethanol terephthalate) (PCT). Combinations comprising at least one of the foregoing polyesters may also be used.

Copolymers comprising alkylene terephthalate repeating ester units with other suitable ester groups may also be useful. Specifically useful ester units may include different alkylene terephthalate units, which can be present in the polymer chain as individual units, or as blocks of poly(alkylene terephthalates). Specifically suitable examples of such copolymers include poly(cyclohexanedimethanol terephthalate)-co-poly (ethylene terephthalate), abbreviated as PETG where the polymer comprises greater than or equal to 50 mole % of poly(ethylene terephthalate), and abbreviated as PCTG where the polymer comprises greater than 50 mole % of poly(cyclohexanedimethanol terephthalate).

Suitable poly(cycloalkylene diester)s may include poly (alkylene cyclohexanedicarboxylate)s. Of these, a specific example is poly(1,4-cyclohexane dimethanol-1,4-cyclohexanedicarboxylate) (PCCD), having recurring units of formula (9):

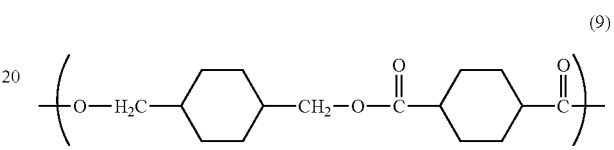

wherein, as described using formula (8), D is a dimethylene cyclohexane group derived from cyclohexane dimethanol, and T is a cyclohexane ring derived from cyclohexanedicarboxylate or a chemical equivalent thereof and is selected from the cis- or trans-isomer or a mixture of cis- and trans- isomers thereof.

The polycarbonate and polyester may be used in a weight ratio of 1:99 to 99:1, specifically 10:90 to 90:10, and more specifically 30:70 to 70:30, depending on the function and properties desired.

It is desirable for such a polyester and polycarbonate blend to have a melt volume rate of about 5 to about 150 cc/10 min., specifically about 7 to about 125 cc/10 min, more specifically about 9 to about 110 cc/10 min, and still more specifically about 10 to about 100 cc/10 min., measured at 300° C. and a load of 1.2 kilograms according to ASTM D1238-04. The above polyesters with a minor amount, e.g., from about 0.5 to about 10 percent by weight, of units derived from an aliphatic diacid and/or an aliphatic polyol to make copolyesters.

The polycarbonate may also comprise a polysiloxane-polycarbonate copolymer, also referred to as a polysiloxane-polycarbonate. The polysiloxane (also referred to herein as "polydiorganosiloxane") blocks of the copolymer comprise repeating siloxane units (also referred to herein as "diorganosiloxane units") of formula (10):

wherein each occurrence of R is same or different, and is a $C_{1-13}$ monovalent organic radical. For example, R may independently be a $C_1$-$C_{13}$ alkyl group, $C_1$-$C_{13}$ alkoxy group, $C_2$-$C_{13}$ alkenyl group, $C_2$-$C_{13}$ alkenyloxy group, $C_3$-$C_6$ cycloalkyl group, $C_3$-$C_6$ cycloalkoxy group, $C_6$-$C_{14}$ aryl group, $C_6$-$C_{10}$ aryloxy group, $C_7$-$C_{13}$ arylalkyl group, $C_7$-$C_{13}$ arylalkoxy group, $C_7$-$C_{13}$ alkylaryl group, or $C_7$-$C_{13}$ alkylaryloxy group. The foregoing groups may be fully or partially halogenated with fluorine, chlorine, bromine, or iodine, or a combination thereof. Combinations of the foregoing R groups may be used in the same copolymer.

The value of E in formula (10) may vary widely depending on the type and relative amount of each component in the thermoplastic composition, the desired properties of the composition, and like considerations. Generally, E may have an average value of 2 to 1,000, specifically 2 to 500, and more specifically 5 to 100. In one embodiment, E has an average value of 10 to 75, and in still another embodiment, E has an average value of 40 to 60. Where E is of a lower value, e.g., less than 40, it may be desirable to use a relatively larger amount of the polycarbonate-polysiloxane copolymer. Conversely, where E is of a higher value, e.g., greater than 40, it may be necessary to use a relatively lower amount of the polycarbonate-polysiloxane copolymer.

A combination of a first and a second (or more) polysiloxane-polycarbonate copolymer may be used, wherein the average value of E of the first copolymer is less than the average value of E of the second copolymer.

In one embodiment, the polydiorganosiloxane blocks are provided by repeating structural units of formula (11):

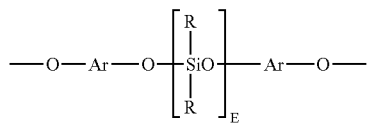

(11)

wherein E is as defined above; each R may independently be the same or different, and is as defined above; and each Ar may independently be the same or different, and is a substituted or unsubstituted $C_6$-$C_{30}$ arylene radical, wherein the bonds are directly connected to an aromatic moiety. Suitable Ar groups in formula (11) may be derived from a $C_6$-$C_{30}$ dihydroxyarylene compound, for example a dihydroxyarylene compound of formula (3), (4), (6), or (7) above. Combinations comprising at least one of the foregoing dihydroxyarylene compounds may also be used. Specific examples of suitable dihydroxyarylene compounds are 1,1-bis(4-hydroxyphenyl) methane, 1,1-bis(4-hydroxyphenyl) ethane, 2,2-bis(4-hydroxyphenyl) propane, 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-1-methylphenyl) propane, 1,1-bis(4-hydroxyphenyl) cyclohexane, bis(4-hydroxyphenyl sulphide), and 1,1-bis(4-hydroxy-t-butylphenyl) propane. Combinations comprising at least one of the foregoing dihydroxy compounds may also be used.

Units of formula (11) may be derived from the corresponding dihydroxy compound of formula (12):

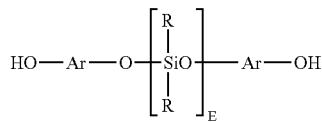

(12)

wherein R, Ar, and E are as described above. Compounds of formula (12) may be obtained by the reaction of a dihydroxyarylene compound with, for example, an alpha, omega-bisacetoxypolydiorangonosiloxane under phase transfer conditions.

In another embodiment, polydiorganosiloxane blocks comprise units of formula (13):

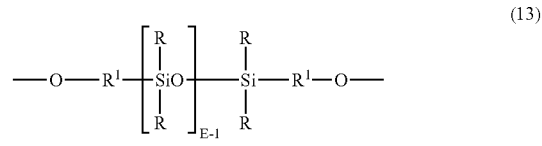

(13)

wherein R and E are as described above, and each occurrence of $R^1$ is independently a divalent $C_1$-$C_{30}$ alkylene, and wherein the polymerized polysiloxane unit is the reaction residue of its corresponding dihydroxy compound. In a specific embodiment, the polydiorganosiloxane blocks are provided by repeating structural units of formula (14):

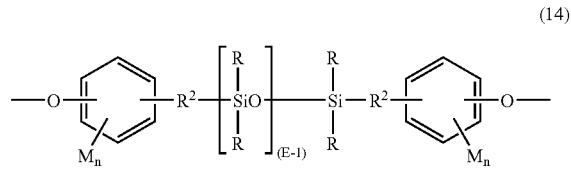

(14)

wherein R and E are as defined above. Each $R^2$ in formula (14) is independently a divalent $C_2$-$C_8$ aliphatic group. Each M in formula (14) may be the same or different, and may be a halogen, cyano, nitro, $C_1$-$C_8$ alkylthio, $C_1$-$C_8$ alkyl, $C_1$-$C_8$ alkoxy, $C_2$-$C_8$ alkenyl, $C_2$-$C_8$ alkenyloxy group, $C_3$-$C_8$ cycloalkyl, $C_3$-$C_8$ cycloalkoxy, $C_6$-$C_{10}$ aryl, $C_6$-$C_{10}$ aryloxy, $C_7$-$C_{12}$ arylalkyl, $C_7$-$C_{12}$ arylalkoxy, $C_7$-$C_{12}$ alkylaryl, or $C_7$-$C_{12}$ alkylaryloxy, wherein each n is independently 0, 1, 2, 3, or 4.

In one embodiment, M is bromo or chloro, an alkyl group such as methyl, ethyl, or propyl, an alkoxy group such as methoxy, ethoxy, or propoxy, or an aryl group such as phenyl, chlorophenyl, or tolyl; $R^2$ is a dimethylene, trimethylene or tetramethylene group; and R is a $C_{1-8}$ alkyl, haloalkyl such as trifluoropropyl, cyanoalkyl, or aryl such as phenyl, chlorophenyl or tolyl. In another embodiment, R is methyl, or a mixture of methyl and trifluoropropyl, or a mixture of methyl and phenyl. In still another embodiment, M is methoxy, n is one, $R^2$ is a divalent $C_1$-$C_3$ aliphatic group, and R is methyl.

Units of formula (14) may be derived from the corresponding dihydroxy polydiorganosiloxane (15):

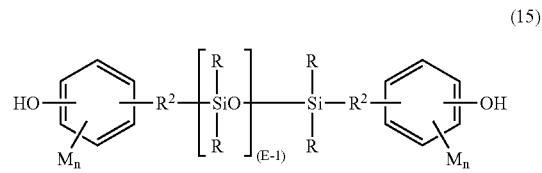

(15)

wherein R, D, M, $R^2$, and n are as described above. Such dihydroxy polysiloxanes can be made by effecting a platinum catalyzed addition between a siloxane hydride of formula (16):

wherein R and E are as previously defined, and an aliphatically unsaturated monohydric phenol. Suitable aliphatically unsaturated monohydric phenols included, for example, eugenol, 2-allylphenol, 4-allyl-2-methylphenol, 4-allyl-2-phenylphenol, 4-allyl-2-bromophenol, 4-allyl-2-t-butoxyphenol, 4-phenyl-2-phenylphenol, 2-methyl -4-propylphenol, 2-allyl-4,6-dimethylphenol, 2-allyl-4-bromo-6-methylphenol, 2-allyl-6-methoxy-4-methylphenol and 2-allyl-4,6-dimethylphenol. Mixtures comprising at least one of the foregoing may also be used.

The polysiloxane-polycarbonate may comprise 50 to 99 wt % of carbonate units and 1 to 50 wt % siloxane units. Within this range, the polysiloxane-polycarbonate copolymer may comprise 70 to 98 wt %, specifically 75 to 97 wt % of carbonate units and 2 to 30 wt %, specifically 3 to 25 wt % siloxane units.

In an embodiment, the polysiloxane-polycarbonate may comprise polysiloxane units, and carbonate units derived from bisphenol A, e.g., the dihydroxy compound of formula (3) in which each of $A^1$ and $A^2$ is p-phenylene and $Y^1$ is isopropylidene. Polysiloxane-polycarbonates may have a weight average molecular weight of 2,000 to 100,000, specifically 5,000 to 50,000 as measured by gel permeation chromatography using a crosslinked styrene-divinyl benzene column, at a sample concentration of 1 milligram per milliliter, and as calibrated with polycarbonate standards.

The polysiloxane-polycarbonate can have a melt volume flow rate, measured at 300° C./1.2 Kg, of 1 to 50 cubic centimeters per 10 minutes (cc/10 min), specifically 2 to 30 cc/10 min. Mixtures of polysiloxane-polycarbonates of different flow properties may be used to achieve the overall desired flow property.

The thermoplastic compositions further comprise an aryl carboxylate end-capped polycarbonate of formula (17):

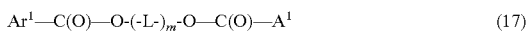  (17)

wherein each $Ar^1$ is independently an aryl group. Suitable groups include $C_6$-$C_{20}$ aryl group, or substituted $C_6$-$C_{20}$ aryl group. When present, substituents on the $Ar^1$ groups may include, for example, nitro, cyano, hydroxy, thio, halogen (fluoro, chloro, bromo, iodo), $C_1$-$C_{12}$ alkyl, $C_1$-$C_{12}$ alkyl ether, $C_1$-$C_{12}$ acyl, $C_1$-$C_{12}$ acyloxy, $C_6$-$C_{20}$ aryl, or $C_6$-$C_{20}$ aryloxy. Examples of suitable $Ar^1$ groups include phenyl, 2-methylphenyl, 3-methylphenyl, 4-methylphenyl, 3,5-dimethylphenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 3,4,5-trimethylphenyl, 2,4,6-trimethylphenyl, 4-ethyl phenyl, 4-butyl phenyl, 4-tert-butyl-phenyl, 2-trifluoromethylphenyl, 4-trifluoromethylphenyl, 4-acetylphenyl, 4-acetoxyphenyl, 4-methoxyphenyl, 4-tert-butoxyphenyl, 4-fluorophenyl, 4-chlorophenyl, 4-bromophenyl, naphthyl, $C_1$-$C_{12}$ alkyl-substituted naphthyl, $C_1$-$C_{12}$ alkyl ether-substituted naphthyl, halogen-substituted naphthyl, and the like.

Also in formula (17), $-(-L-)_m-$ is a polycarbonate linking group comprising m units of linking unit L, wherein m is at least one. In an embodiment, L is a carbonate unit of formula (1), and m is 1 to 500. In another embodiment, polycarbonate linking group $-(-L-)_m-$ may comprise additional L units including ester units of formula (8), poly(arylene ether) units, soft block units, or a combination comprising at least one of these, wherein m is 2 to 500, and wherein at least one L is a carbonate unit. Thus, in addition to carbonate units, L may include poly(arylene ether) units of formula (18):

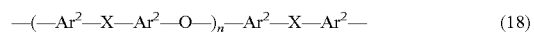  (18)

wherein n is 0 to 200, and wherein each $Ar^2$ is independently a substituted or unsubstituted $C_6$-$C_{20}$ arylene group. When present, substituents on the $Ar^2$ groups may include, for example, nitro, cyano, hydroxy, thio, halogen (fluoro, chloro, bromo, iodo), $C_1$-$C_{12}$ alkyl, $C_1$-$C_{12}$ alkyl ether, $C_1$-$C_{12}$ acyl, $C_1$-$C_{12}$ acyloxy, $C_6$-$C_{20}$ aryl, or $C_6$-$C_{20}$ aryloxy. Examples of suitable arylene groups include 1,2-phenylene, 1,3-phenylene, 1,4-phenylene, 2-methyl-1,4-phenylene, 5-methyl-1,3-phenylene, 2-methoxy-1,4-phenylene, 2,5-dimethyl-1,4-phenylene, 2,6-dimethyl-1,4-phenylene, 2,3,5,6-tetramethyl-1,4-phenylene, 1,4-naphthalenediyl, 1,5-naphthalenediyl, 2,6-naphthalenediyl, and the like.

Also in formula (18), X is a bridging radical having one or two atoms that separate the $Ar^2$ groups. In an exemplary embodiment, one atom separates the $Ar^2$ groups. Illustrative non-limiting examples of radicals of this type are —O—, —S—, —S(O)—, —S(O$_2$)—, —C(O)—, methylene, cyclohexyl-methylene, 2-[2.2.1]-bicycloheptylidene, ethylidene, isopropylidene, neopentylidene, isatinylene, spirobiindanylene, phthalimidine, cyclohexylidene, cyclopentadecylidene, cyclododecylidene, and adamantylidene.

Poly(arylene ether) groups of formula (18) may be derived from the corresponding dihydroxy compound of formula (19):

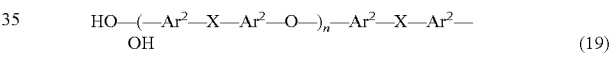  (19)

wherein $Ar^2$, X, and n are as described above. Examples of suitable dihydroxy poly(arylene ether) compounds include, but are not limited to, polyalkylene-arylene ethers such as poly(bisphenol-A ether); poly(arylene ether) sulfones such as poly(diphenylether)sulfone; poly(arylene ether) sulfides such as poly(diphenylene ether) sulfide; and the like, and a combination comprising at least one of these.

In another further embodiment, in addition to the carbonate units, L may comprise a soft-block unit. As used herein, the term "soft block" is used to describe an oligomeric or polymeric unit having a Tg lower than that of the polycarbonate and/or polyester units with which it forms a copolymer. Soft blocks comprising soft block units, where used, desirably have thermal stability to melt processing at temperatures of at least 240° C. Soft block units, when copolymerized with carbonate units, ester units, or a combination comprising at least one of these, may form a copolymer having alternating, random, or block arrangements of the soft block unit. Suitable soft block units include polysiloxane units, polyalkylene oxide units, poly(alkylene ester) units, polyolefin units, or a combination comprising at least one of these.

Where linking group L comprises a soft block unit, the soft block unit may be derived from an oligomeric or polymeric dihydroxy compound having the general formula HO-G-OH, where G is the soft block unit. Examples of suitable oligomeric or polymeric dihydroxy compounds from which the soft block units are derived include, but are not limited to, dihydroxy-capped polydiorganosiloxanes of formulas (12) and (15); dihydroxy poly(alkylene oxide)s such as polyethylene glycol, polypropylene glycol, poly (ethylene glycol)- co-(propylene glycol), and the like; hydroxy end-capped poly (alkylene ester)s such as poly(ethylene terephthalate), poly (1,4-butylene terephthalate), poly(1,4-dimethylene cyclohexane terephthalate), poly(1,4-dimethylene cyclohexane-bis 1,4-cyclohexanedicarboxylate), poly(ethylene terephthalate)-co-(1,4-dimethylene cyclohexane terephthalate), and the like; polyolefins such as dihydroxy derivatives of polyethylene, polypropylene, poly(ethylene-co-propylene), and the like; and a combination comprising at least one of the foregoing. Specifically useful examples of suitable dihydroxy compounds include bisphenol-A, dihydroxy-capped poly(isophthalate-terephthalate resorcinol) esters, dihydroxy-capped poly(isophthalate-terephthalate bisphenol-A) esters, eugenol-capped polydimethylsiloxane, bisphenol-A capped polydimethylsiloxane, dihydroxy-capped poly (bisphenol-A) ether, ethylene glycol-capped poly(ethylene terephthalate), poly(ethylene glycol), and the like, or a combination comprising at least one of the foregoing.

A polyarylene block or soft block, where used, may be present along with carbonate units in a weight ratio of 50:50 to 1:99, specifically 40:60 to 2:98, and still more specifically 30:70 to 3:97.

Thus, in an embodiment, suitable aryl carboxylate end-capped polycarbonates of formula (17) include aryl carboxylate end-capped homopolycarbonate, aryl carboxylate end-capped copolycarbonate, aryl carboxylate end-capped polyester-polycarbonate, aryl carboxylate end-capped polysiloxane-polycarbonate, aryl carboxylate end-capped polysiloxane-co-(polyester-polycarbonate), aryl carboxylate end-capped poly(arylene ether)-co-polycarbonate, aryl carboxylate end-capped poly(arylene ether)-co-(polyester-polycarbonate), aryl carboxylate end-capped poly(alkylene ester)-co-polycarbonate, aryl carboxylate end-capped poly (alkylene ester)-co-(polyester-polycarbonate), aryl carboxylate end-capped poly(alkylene ether)-co-polycarbonate, aryl carboxylate end-capped poly(alkylene ether)-co-(polyester-polycarbonate), aryl carboxylate end-capped polyolefin-co-polycarbonate, aryl carboxylate end-capped poly(olefin)-co-(polyester-polycarbonate), or a combination comprising at least one of these. In an exemplary embodiment, an aryl carboxylate end-capped polycarbonate is a benzoate end-capped poly(bisphenol-A carbonate).

Aryl carboxylate end-capped polycarbonates of formula (17) may be derived from the condensation reaction of a dihydroxy compound, a reactive derivative of an aryl carboxylic acid, and a reactive carbonyl compound, such as for example phosgene; a dialkyl- or diarylchloroformate; a phosgene derivative such as diphosgene or triphosgene; or the like. The aryl carboxylate end-capped polycarbonate may generally be prepared by aqueous biphasic reaction similar to that described hereinabove for the preparation of polycarbonates, polyesters, and polyester-polycarbonates. Specifically, in the method of preparing the aryl carboxylate end-capped polycarbonates herein, the aryl carboxylic acid halide is included as a chain stopper.

Suitable dihydroxy compounds from which the aryl carboxylate end-capped polycarbonate may be derived include those having the formula HO—$R^1$—OH, including dihydroxy aromatic compounds of formulas (3), (4), (6), (7), and examples described therein; dihydroxy poly(arylene ether)s of formula (19), as described above; and dihydroxy soft blocks of general formula HO-G-OH, also as described above, and a combination comprising at least one of these.

In an embodiment, derivatives of aryl carboxylic acids may also be used as chain stoppers. Suitable derivatives of aryl carboxylic acids may include, for example, aryl carboxylic acid halides including acid chlorides, bromides, and fluorides; anhydrides; and mixed anhydrides. Of these, aryl carboxylic acid halides, especially aryl carboxylic acid chlorides, are specifically useful. Suitable aryl carboxylic acid halides include those derived from $C_6$-$C_{30}$ aryl carboxylic acids and substituted $C_6$-$C_{30}$ aryl carboxylic acids. Suitable substituents on the $Ar^1$ groups may include, for example, nitro, cyano, hydroxy, thio, halogen (fluoro, chloro, bromo, iodo), $C_1$-$C_{12}$ alkyl, $C_1$-$C_{12}$ alkyl ether, $C_1$-$C_{12}$ acyl, $C_1$-$C_{12}$ acyloxy, $C_6$-$C_{20}$ aryl, or $C_6$-$C_{20}$ aryloxy. Examples of aryl carboxylic acid halides that may be used include, but are not limited to, benzoyl chloride, 2-methylbenzoyl chloride, 3-methylbenzoyl chloride, 4-methylbenzoyl chloride, 3,5-dimethylbenzoyl chloride, 2,3-dimethylbenzoyl chloride, 2,4-dimethylbenzoyl chloride, 2,5-dimethylbenzoyl chloride, 2,6-dimethylbenzoyl chloride, 2,3,4-trimethylbenzoyl chloride, 2,3,5-trimethylbenzoyl chloride, 3,4,5-trimethylbenzoyl chloride, 2,4,6-trimethylbenzoyl chloride, 4-ethyl benzoyl chloride, 4-n-butyl benzoyl chloride, 4-tert-butylbenzoyl chloride, 4-acetylbenzoyl chloride, 4-acetoxybenzoyl chloride, 4-methoxybenzoyl chloride, 4-tert-butoxybenzoyl chloride, 2-fluorobenzoyl chloride, 4-fluorobenzoyl chloride, 4-chlorobenzoyl chloride, 4-bromobenzoyl chloride, 2-trifluoromethylbenzoyl chloride, 3-trifluoromethylbenzoyl chloride, 4-trifluoromethylbenzoyl chloride, naphthoyl chloride, $C_{1-12}$ alkyl naphthoyl chlorides, $C_{1-12}$ alkyloxy naphthoyl chlorides, halo-substituted naphthoyl chlorides, and the like. Of the foregoing aryl carboxylic acid derivatives, benzoyl chloride is specifically useful. The aryl carboxylic acid halide chain stoppers may be used alone or as a combination comprising at least one of the foregoing aryl carboxylic acid halide chain stoppers. Alternatively, the aryl carboxylic acid halide chain stoppers may be used in combination with at least one of the aforementioned mono-phenolic compounds, mono-chloroformates, and/or sulfonic acid derivatives.

The condensation reaction between the aryl carboxylic acid halide and dihydroxy compounds may generally be carried out in a single phase using an organic solvent, in the presence of a base. Alternatively, the condensation reaction may be carried out in a biphasic reaction using an organic solvent and water, in the presence of a base.

In an embodiment, suitable methods for forming an aryl carboxylate end-capped polycarbonate are disclosed. In one method, for example, a dihydroxy compound, aryl carboxylic acid halide, a base, solvent, and activated carbonyl compound are combined in a medium, wherein the pH of the medium is maintained at about 9 to about 11 while combining and reacting, and is biphasic, having a solvent phase and an aqueous phase. Suitable bases include, for example, triethylamine, sodium hydroxide, sodium carbonate, sodium bicarbonate, sodium acetate, sodium gluconate, sodium citrate, sodium tartrate, and the like, or a combination comprising at least one of these. Maintaining pH may also be done by addition of a suitable base, for example sodium hydroxide as a concentrated solution in water, as needed during the reaction. In an embodiment, the activated carbonyl compound is phosgene. In another embodiment, the dihydroxy compound, aryl carboxylic acid halide, and base are pre-reacted in the biphasic solution prior to addition of the activated carbonyl compound. In a specific embodiment, pre-reacting is done at a pH of about 7.5 to about 11.5, specifically at a pH of about 7.5 to about 11, more specifically at a pH of about 7.8 to about 11 more specifically at a pH of about 8 to about 10.5. In another embodiment, pre-reacting is done for a time of 1 to 60 minutes, specifically 2 to 30 minutes, more specifically 3 to 20 minutes, and still more specifically 4 to 15 minutes. In another method, for example, a phase transfer catalyst having the formula $(R^3)_4Q^+X$, wherein $R^3$, Q, and X are as defined above, may be included. An example of a specifically useful phase transfer catalyst is methyl tri-n-butyl ammonium chloride. In another method, for example, a suitable dihydroxy compound comprises a dihydroxy aromatic compound, a dihydroxy. poly(arylene ether), a dihydroxy soft-block compound, or a combination comprising at least one of the foregoing. In an embodiment, where a combination is used, the dihydroxy poly(arylene ether) or dihydroxy soft block is used to displace a portion of the dihydroxy aromatic compound charge. In another further method, for example, the monohaloformate, bis-haloformate, or a combination comprising mono- and bis-haloformates of the dihydroxy polyarylene or dihydroxy soft-block compounds are used. The resulting aryl carboxylate end-capped polycarbonate may be isolated by precipitation from the medium by addition to a non-solvent. Proportions, types, and amounts of the reaction ingredients may be determined and selected by one skilled in the art to provide aryl carboxylate end-capped polycarbonates having desirable physical properties including but not limited to, for example, suitable molecular weight, MVR, and glass transition temperature. In an example of a specific embodiment, the dihydroxy compound used is bisphenol-A. In another example of a specific embodiment, a suitable aryl carboxylic acid halide is benzoyl chloride. In another example of a specific embodiment, an aryl carboxylate end-capped polycarbonate made by the above method is a benzoate end-capped poly(bisphenol-A carbonate). In an embodiment, the glass transition temperature of an aryl carboxylate end-capped polycarbonate is comparable to that of a similar polycarbonate polymer of the same composition but without aryl carboxylate end groups. In an exemplary embodiment, benzoate end-capped poly(bisphenol-A carbonate) prepared by the above method has a Tg of 145-150° C., comparable to that of a similar poly(bisphenol-A carbonate) prepared with aromatic carbonate end groups. The aryl carboxylate end-capped polycarbonate so prepared may have a polydispersity (Mw/Mn) of less than 4.5.

Biphasic condensation of dihydroxy compounds and aryl carboxylic acid halides may result in an inefficient condensation of the dihydroxy compound and the aryl carboxylic acid halide. Such inefficiencies may in turn lead to increased hydrolysis of the aryl carboxylic acid halide to the non-reacting aryl carboxylic acid halide, a low number of aryl carboxylate end groups in the aryl carboxylate end-capped polycarbonate, and the presence of substantial amounts of unreacted aryl carboxylic acid halide of greater than 10% by weight of the initial charge. In addition, in the presence of an activated carbonyl compound such as phosgene, the competing rates of conversion between the phosgene and the aryl carboxylic acid halide during phosgenation may lead to variability in the properties of the resulting polymer, such as for example poor molecular weight control, the presence of low molecular weight monomers and oligomers, and variable polydispersity. Such variations in turn may affect other associated polymer properties such as melt flow and/or-viscosity stability, impact strength, processability, and other physical properties.

In an advantageous feature of the above-described method of preparing the aryl carboxylate end-capped polycarbonate, it has been found that condensing the dihydroxy compound and aryl carboxylic acid halide prior to effecting condensation with the activated carbonyl compound, referred to herein as "pre-condensing" the dihydroxy compound and aryl carboxylic acid halide, provides a more efficient condensation of the aryl carboxylic acid halide with the dihydroxy compound, and further provides better molecular weight and polydispersity control of the aryl carboxylate end-capped polycarbonate than would be obtained in the absence of a pre-condensation of these components. It is believed that the rate of condensation of the aryl carboxylic acid halide with the dihydroxy compound is slower than the rate of condensation of the activated carbonyl compound and dihydroxy compound. Pre-condensation can substantially reduce the concentration of the aryl carboxylic acid halide present during phosgenation, thereby reducing the competition between reaction rates of the aryl carboxylic acid halide and the phosgene toward the dihydroxy compound. In an embodiment, the aryl carboxylate end-capped polycarbonate is a polycarbonate prepared by a method wherein an aryl carboxylic acid halide chain stopper is pre-condensed with a dihydroxy compound prior to phosgenation. In another embodiment, aryl carboxylic acid halide may be present in the biphasic reaction medium after polymerization of the dihydroxy compound is complete, in an amount of less than or equal to 50 wt %, more specifically less than or equal to 25 wt %, more specifically less than or equal to 10 wt %, still more specifically less than or equal to 5 wt %, of the initial charge of aryl carboxylic acid halide. In another advantageous feature, pre-condensing aryl carboxylic acid halide with dihydroxy compound allows for improved pH control in the medium during addition of the active carbonyl compound. The improved pH control can allow for better control of the rate of condensation of the activated carbonyl compound and can also result in improved control of molecular weight and polydispersity.

The aryl carboxylate end-capped polycarbonate is used in the thermoplastic composition in an amount effective to inhibit yellowing of the polycarbonate upon irradiation, in particular exposure to gamma radiation. Effective amounts are readily determined by one of ordinary skill in the art, and will vary depending upon the type of resin(s) used in the composition, the type and amount of other additives, and the intended use of the composition. The aryl carboxylate end-capped polycarbonates are generally completely miscible with polycarbonates, and possess equivalent physical and rheological properties to comparable compositions without aryl carboxylate end groups.

A useful amount of aryl carboxylate end-capped polycarbonate for may be determined according to the molar quantity of the aryl carboxylate end-group present in the thermoplastic composition. This amount can correlate to the amount of aryl carboxylic acid halide initially used to prepare the aryl carboxylate end-capped polycarbonate. The amount of aryl carboxylate end-group may be determined after isolation of the polymer for the aryl carboxylate end-capped polycarbonate, by using end group analysis methods such as, for example, proton nuclear magnetic resonance spectrometry ($^1$H NMR), and/or by calculating the number of end groups from the number-averaged molecular weight Mn (as determined using a suitable molecular weight determination method including, but not limited to gel permeation chromatography (GPC), dynamic light scattering, vapor phase osmometry, or other suitable methods). As disclosed herein, the aryl carboxylate end-capped polycarbonate has a number averaged molecular weight (Mn) of 1,000 to 100,000, specifically 2,000 to 75,000, more specifically 5,000 to 50,000, and still more specifically 7,500 to 25,000, as determined by GPC using a crosslinked styrene-divinylbenzene column calibrated using polystyrene or polycarbonate standards, and a sample concentration of 1 milligram per milliliter (mg/ml). The aryl carboxylate end-capped polycarbonate may also have a weight averaged molecular weight (Mw) of 2,000 to 200,000, specifically 4,000 to 150,000, more specifically 10,000 to 100,000, and still more specifically 15,000 to 50,000, as determined by GPC using a crosslinked styrene-divinylbenzene column calibrated using polystyrene or polycarbonate standards, and a sample concentration of 1 mg/ml.

In general, aryl carboxylate end groups are present in the aryl carboxylate end-capped polycarbonate an amount of 0.01 to 10 mole-percent (mol %), more specifically 0.1 to 8 mol %, even more specifically 1 to 7.5 mol %, and even more specifically 2 to 7 mol %, of the isolated aryl carboxylate end-capped polycarbonate. Amounts lower than 0.01 mol % may not be effective, while amounts greater than 10 mol % may adversely affect one or more physical and/or mechanical properties of the thermoplastic composition.

In general, an effective molar equivalent amount of aryl carboxylate end group of the aryl carboxylate end-capped polycarbonate, is present in the thermoplastic composition in an amount of 0.01 to 500 millimoles per kilogram (mmol/Kg), based on the combined weight of the polycarbonate resin and the aryl carboxylate end-capped polycarbonate, more specifically 0.1 to 400 mmol/Kg, even more specifically 1 to 300 mmol/Kg of the combined weight of the polycarbonate resin and the aryl carboxylate end-capped polycarbonate. Amounts lower than 0.01 mmol/Kg may not be effective, while amounts greater than about 500 mmol/Kg can adversely affect one or more physical and/or mechanical properties of the thermoplastic composition. In an embodiment, a masterbatch composition comprising polycarbonate that is not aryl carboxylate end-capped, and levels of 5 to 500 mmol/Kg of aryl carboxylate end-capped polycarbonate may be prepared, wherein the masterbatch is further combined with polycarbonate and/or other polymer to form the thermoplastic composition.

In an unexpected and advantageous feature, however, it has been found that aryl carboxylate end-capped polycarbonate, used alone or as a combination with other polymers, is effective to prevent yellowing upon exposure to radiation, including gamma radiation. In an embodiment, the aryl carboxylate end-capped polycarbonate is used in an amount of 0.1 to 100 wt %, specifically 1 to 80 wt %, more specifically 2 to 50 wt %, still more specifically 5 to 40 wt %, and still more specifically 9 to 30 wt %, based on the total weight of the polycarbonate that is not aryl carboxylate end-capped, and aryl carboxylate end-capped polycarbonate, with the proviso that the amount and type of aryl carboxylate end-capped polycarbonate used is selected so that the overall concentration of aryl carboxylate end group is less than or equal to a molar concentration of 500 millimoles per kilogram (mmol/Kg), and is greater than or equal to 0.01 mmol/Kg, of the total weight of the polycarbonate that is not aryl carboxylate end-capped, and aryl carboxylate end-capped polycarbonate.

The thermoplastic composition may further comprise an ionizing radiation stabilizing additive. Exemplary ionizing radiation stabilizing additives include certain aliphatic alcohols, aromatic alcohols, aliphatic diols, aliphatic ethers, esters, diketones, alkenes, thiols, thioethers and cyclic thioethers, sulfones, dihydroaromatics, diethers, nitrogen compounds, or a combination comprising at least one of the foregoing. Alcohol-based stabilizing additives may be selected from mono, di-, or polysubstituted alcohols, and can be straight, branched, cyclic and/or aromatic. Suitable aliphatic alcohols may include alkenols with sites of unsaturation, examples of which include 4-methyl-4-penten-2-ol, 3-methyl-pentene-3-ol, 2-methyl-4-penten-2-ol, 2,4-dimethyl-4-penten-2-ol, 2-phenyl-4-penten-2-ol, and 9-decen-1-ol; tertiary alcohols including 3-hydroxy-3-methyl-2-butanone, 2-phenyl-2-butanol, and the like; hydroxy-substituted tertiary cycloaliphatics such as 1-hydroxy-1-methyl-cyclohexane; and hydroxymethyl aromatics having an aromatic ring with carbinol substituents such as a methylol group (—CH$_2$OH) or a more complex hydrocarbon group such as (—CRHOH) or (—CR$_2$OH), wherein R is straight chain C$_1$-C$_{20}$ alkyl or branched C$_1$-C$_{20}$ alkyl. Exemplary hydroxy carbinol aromatics include benzhydrol, 2-phenyl-2-butanol, 1,3-benzenedimethanol, benzyl alcohol, 4-benzyloxy-benzyl alcohol, and benzyl-benzyl alcohol.

Useful classes of ionizing radiation stabilizing additives are di- and polyfunctional aliphatic alcohols, also referred to as aliphatic diols and aliphatic polyols. Specifically useful are aliphatic diols of formula (20):

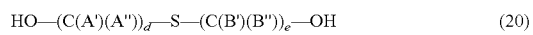

$$HO-(C(A')(A''))_d-S-(C(B')(B''))_e-OH \quad (20)$$

wherein A', A", B', and B" are each independently H or C$_1$-C$_6$ alkyl; S is C$_1$-C$_{20}$ alkyl, C$_2$-C$_{20}$ alkyleneoxy, C$_3$-C$_6$ cycloalkyl, or C$_3$-C$_6$ substituted cycloalkyl; and d and e are each 0 or 1, with the proviso that, when d and e are each 0, S is selected such that both —OH groups are not connected directly to a single common carbon atom.

In formula (20), A', A", B', and B" can each be independently selected from H, methyl, ethyl, n-propyl, isopropyl, n-butyl, sec-butyl, t-butyl, n-pentyl, 2-pentyl, 3-pentyl, isopentyl, neopentyl, n-hexyl, 2-hexyl, 3-hexyl, 2-methyl pentyl, 3-methylpentyl, 2,2-dimethylbutyl, 2,3-dimethylbutyl, and the like, and a combination comprising at least one of the foregoing alkyl groups.

Spacer group S can be selected from methanediyl, ethanediyl, 1,1-ethanediyl, 1,1-propanediyl, 1,2-propanediyl, 1,3-propanediyl, 2,2-propanediyl, 1,1-butanediyl, 1,2-butanediyl, 1,3-butanediyl, 1,4-butanediyl, 2,2-butanediyl, 2,3-butanediyl, 1,1-pentanediyl, 1,2-pentanediyl, 1,3-pentanediyl, 1,4-pentanediyl, 1,5-pentanediyl, 2,2-pentanediyl, 2,3-pentanediyl, 2,4-pentanediyl, 3,3-pentanediyl, 2-methyl-1,1-butanediyl, 3-methyl-1,1-butanediyl, 2-methyl-1,2-butanediyl, 2-methyl-1,3-butanediyl, 2-methyl-1,4-butanediyl, 2-methyl-2,2-butanediyl, 2-methyl-2,3-butanediyl, 2,2-dimethyl-1,1-propanediyl, 2,2-dimethyl-1,2-propanediyl, 2,2-dimethyl-1,3-propanediyl, 3,3-dimethyl-1,1-propanediyl, 3,3-dimethyl-1,2-propanediyl, 3,3-dimethyl-2,2-propanediyl, 1,1-dimethyl-2,3-propanediyl, 3,3-dimethyl-2,2-propanediyl, 1,1-hexanediyl, 1,2-hexanediyl, 1,3-hexanediyl, 1,4-hexanediyl, 1,5-hexanediyl, 1,6-hexanediyl, 2,2-hexanediyl, 2,3-hexanediyl, 2,4-hexanediyl, 2,5-hexanediyl, 3,3-hexanediyl, 2-methyl-1,1-pentanediyl, 3-methyl-1,1-pentanediyl, 2-methyl-1,2-pentanediyl, 2-methyl-1,3-pentanediyl, 2-methyl-1,4-pentanediyl, 2-methyl-2,2-pentanediyl, 2-methyl-2,3-pentanediyl, 2-methyl-2,4-pentanediyl, 2,2-dimethyl-1,1-butanediyl, 2,2-dimethyl-1,2-butanediyl, 2,2-dimethyl-1,3-butanediyl, 3,3-dimethyl-1,1-butanediyl, 3,3-dimethyl-1,2-butanediyl, 3,3-dimethyl-2,2-butanediyl, 1,1-dimethyl-2,3-butanediyl, 3,3-dimethyl-2,2-butanediyl, and the like; isomers of octanediyl, decanediyl, undecanediyl, dodecanediyl, hexadecanediyl, octadecanediyl, icosananediyl, and docosananediyl; and substituted and unsubstituted cyclopropanediyl, cyclobutanediyl, cyclopentanediyl, cyclohexanediyl, wherein substituents may be the points of radical attachment, such as in 1,4-dimethylenecyclohexane, or may include branched and straight chain alkyl, cycloalkyl, and the like. Additionally, the spacer group S may be selected from one or more diradicals comprising polyalkyleneoxy units, such as ethyleneoxy, 1,2-propyleneoxy, 1,3-propyleneoxy, 1,2-butyleneoxy, 1,4-butyleneoxy, 1,6-hexyleneoxy, and the like; and a combination comprising at least one of these.

Specific examples of suitable aliphatic diols include ethylene glycol, propylene glycol, 1,3-propanediol, 1,2-butanediol, 1,4-butanediol, meso-2,3-butanediol, 1,2-pentanediol, 2,3-pentanediol, 1,4-pentanediol, 1,4-hexanediol, and the like; alicyclic alcohols such as 1,3-cyclobutanediol, 2,2,4,4-tetramethylcyclobutanediol, 1,2-cyclopentanediol, 1,2-cyclohexanediol, 1,3-cyclohexanediol, 1,4-cyclohexanediol, 1,4-dimethylolcyclohexane, and the like; branched acyclic diols such as 2,3-dimethyl-2,3-butanediol (pinacol), and 2-methyl-2,4-pentanediol (hexylene glycol); and polyalkyleneoxy-containing alcohols such as polyethylene glycol, polypropylene glycol, block or random poly(ethyleneglycol-co-propyleneglycols), and diols of copolymers containing polyalkyleneoxy-groups. Useful polyols may include polyaryleneoxy compounds such as polyhydroxystyrene; alkyl polyols such as polyvinylalcohol, polysaccharides, and esterified polysaccharides. A combination comprising at least one of the foregoing may also be useful. Specifically suitable diols include 2-methyl-2,4-pentanediol (hexylene glycol), polyethylene glycol, and polypropylene glycol.

Suitable aliphatic ethers may include alkoxy-substituted cyclic or acyclic alkanes such as, for example, 1,2-dialkoxyethanes, 1,2-dialkoxypropanes, 1,3-dialkoxypropanes, alkoxycyclopentanes, alkoxycyclohexanes, and the like. Ester compounds (—COOR) may be useful as stabilizers wherein R may be a substituted or unsubstituted, aromatic or aliphatic, hydrocarbon and the parent carboxy compound may likewise be substituted or unsubstituted, aromatic or aliphatic, and/or mono- or polyfunctional. When present, substituents may include, for example, $C_1$-$C_8$ alkyl, $C_1$-$C_8$ alkyl ether, $C_6$-$C_{20}$ aryl, and the like. Esters which have proven useful include tetrakis(methylene [3,5-di-t-butyl-4-hydroxy-hydrocinnamate])methane, 2,2'-oxamido bis(ethyl-3-(3,5-di-t-butyl-4-hydroxyphenyl) propionate, and trifunctional hindered phenolic ester compounds such as GOODRITE® 3125, available from B. F. Goodrich in Cleveland Ohio.

Diketone compounds may also be used, specifically those having two carbonyl functional groups and separated by a single intervening carbon atoms such as, for example 2,4-pentadione.

Sulfur-containing compounds, suitable for use as stabilizing additives, can include thiols, thioethers and cyclic thioethers. Thiols include, for example, 2-mercaptobenzothiazole; thioethers include dilaurylthiopropionate; and cyclic thioethers include 1,4-dithiane, 1,4,8,11-tetrathiocyclotetradecane. Cyclic thioethers containing more than one thioether group are useful, specifically those having a single intervening carbon between two thioether groups such as in, for example, 1,3-dithiane. The cyclic ring may contain oxygen or nitrogen members.

Aryl or alkyl sulfone stabilizing additives of general structure R—S(O)$_2$-R' may also be used, where R and R' comprise $C_1$-$C_{20}$ alkyl, $C_6$-$C_{20}$ aryl, $C_1$-$C_{20}$ alkoxy, $C_6$-$C_{20}$ aryloxy, substituted derivatives thereof, and the like, and wherein at least one of R or R' is a substituted or unsubstituted benzyl. When present, substituents may include, for example, $C_1$-$C_8$ alkyl, $C_1$-$C_8$ alkyl ether, $C_6$-$C_{20}$ aryl, and the like. An example of a specifically useful sulfone is benzylsulfone.

Alkenes may be used as stabilizing additives. Suitable alkenes may include olefins of general structure RR'C=CR"R''' wherein R, R', R", and R''' may each individually be the same or different and may be selected from hydrogen, $C_1$-$C_{20}$ alkyl, $C_1$-$C_{20}$ cycloalkyl, $C_1$-$C_{20}$ alkenyl, $C_1$-$C_{20}$ cycloalkenyl, $C_6$-$C_{20}$ aryl, $C_6$-$C_{20}$ arylalkyl, $C_6$-$C_{20}$ alkylaryl, $C_1$-$C_{20}$ alkoxy, $C_6$-$C_{20}$ aryloxy and substituted derivatives thereof. When present, substituents may include, for example, $C_1$-$C_8$ alkyl, $C_1$-$C_8$ alkyl ether, $C_6$-$C_{20}$ aryl, and the like. The olefins may be acyclic, exocyclic, or endocyclic. Examples of specifically useful alkenes include 1,2-diphenyl ethane, allyl phenol, 2,4-dimethyl-1-pentene, limonene, 2-phenyl-2-pentene, 2,4-dimethyl-1-pentene, 1,4-diphenyl-1,3-butadiene, 2-methyl-1-undecene, 1-dodecene, and the like, or a combination comprising at least one of the foregoing.

Hydroaromatic compounds may also be useful as stabilizing additives, including partially hydrogenated aromatics, and aromatics in combination with an unsaturated ring. Specific aromatics include benzene and/or naphthalene based systems. Examples of suitable hydroaromatic compounds include indane, 5,6,7,8-tetrahydro-1-naphthol, 5,6,7,8-tetrahydro-2-naphthol, 9,10-dihydro anthracene, 9,10-dihydrophenanthrene, 1-phenyl-1-cyclohexane, 1,2,3,4-tetrahydro-1-naphthol, and the like, or a combination comprising at least one of the foregoing.

Diethers, including hydrogenated and nonhydrogenated, and substituted and unsubstituted pyrans, may also be used as stabilizing additives. When present, substituents may include $C_1$-$C_8$ alkyl, $C_1$-$C_8$ alkyl ether, or $C_6$-$C_{20}$ aryl. The pyrans may have substituents including $C_1$-$C_{20}$ alkyl, $C_6$-$C_{20}$ aryl, $C_1$-$C_{20}$ alkoxy, or $C_6$-$C_{20}$ aryloxy, and which may be positioned on any carbon of the pyran ring. Specifically useful substituent groups include $C_1$-$C_{20}$ alkoxy or $C_6$-$C_{20}$ aryloxy, located on the ring at the six position. Hydrogenated pyrans are specifically useful. Examples of suitable diethers include dihydropyranyl ethers and tetrahydropyranyl ethers.

Nitrogen compounds which may function as stabilizers include high molecular weight oxamide phenolics, for example, 2,2-oxamido bis-[ethyl 3-(3,5-di-tert-butyl-4-hydroxyphenyl)propionate], high molecular weight oxalic anilides and their derivatives, and amine compounds such as thiourea.

Ionizing radiation stabilizing additives are typically used in amounts of 0.001 to 1 wt %, specifically 0.005 to 0.75 wt %, more specifically 0.01 to 0.5 wt %, and still more specifically 0.05 to 0.25 wt %, based on the total weight of the polycarbonate that is not aryl carboxylate end-capped, and aryl carboxylate end-capped polycarbonate. In an embodiment, a specifically suitable ionizing radiation stabilizing additive is an aliphatic diol.

As discussed above, when exposed to gamma radiation, polycarbonates become yellowed in color, with the degree of yellowness increasing with increasing exposure dose of the gamma radiation. At sufficiently high radiation doses, the yellow color may become sufficiently dark that an article prepared from the polycarbonate is compromised in its usefulness. Likewise, with increasing gamma radiation doses, transparency decreases. Blue and/or violet colorants have also been added to polycarbonate compositions in order to offset the yellowness resulting from the sterilization, such that compositions comprising a colorant and articles molded from them may be visibly blue or violet shaded. However, color compensation may not be effective for obtaining colorless parts as the dose of ionizing radiation is increased. In addition, the amount of colorant added to the resin is often selected for a given radiation dose, and thus variation of exposure dose due to process variability or re-sterilization may cause visible color differences between sterilized articles.

While it is not required to provide an explanation of how an invention works, such theories may be useful to for the purposes of better helping the reader to comprehend the invention. Thus, it is to be understood that the claims are not to be limited by the following theory of operation. It is believed that exposure to gamma radiation generates free radical breakdown products of the polycarbonate which can react to form species with extended pi-bond conjugation, and that therefore have a yellow color. Stabilizers can be included in the polycarbonate and used to stabilize or react with these radical species, thus slowing the degradation of polycarbonates, but none appear to be sufficiently active to completely prevent yellowing. The yellowness index of an article prepared from a polycarbonate having a prior art ionizing radiation stabilizing additive alone after exposure to a total gamma radiation dose of 81 kGy is typically greater than about 50, compared with a yellowness index value of less than 1 for the composition before exposure. Similarly, the loss in transparency of a polycarbonate stabilized in this way and treated with the same gamma radiation dose can be greater than or equal to about 15%.

The use of other types of stabilizers, such as those based on photoacid generators that produce sulfonic acids, in particular monofunctional photoacid generators or difunctional photoacid generators having straight-chain (i.e., unbranched) alkyl or polyether groups that produce sulfonic acids (1 or 2 equivalents of acid per molecule of photoacid generator) have been found to require loadings of the stabilizer in excess of 0.5% by weight of the composition. Increased amounts of generated acid can lead to the formation of other breakdown products in the polycarbonate, thus potentially causing additional degradation of the polycarbonate and mitigating the effectiveness of the stabilizer. Additives having aromatic or benzylic oxy and/or carbonyl groups, and with or without alcohol functional groups present, have been included with such prior art mono- and di-functional photoacid generators to improve their performance. However, the use of such additives is not desirable for various reasons of cost, volatility, and concerns about handling, specifically for odor threshold and workplace exposure. Brominated compounds such as, for example, brominated bisphenol A, have also been found to be useful for reducing yellowing of polycarbonate compounds. However, concerns about the environmental impacts of halides such as bromine make this class of compounds less desirable to use.

Surprisingly, it has been found that a polycarbonate that is not aryl carboxylate end-capped, and an aryl carboxylate end-capped polycarbonate as described herein can be used to make a thermoplastic composition that has significantly improved resistance to yellowing upon exposure to gamma radiation. The presence of the aryl carboxylate end-capped polycarbonate provides a high degree of stability in a thermoplastic composition comprising polycarbonate upon exposure to gamma radiation, per unit of aryl carboxylate end-capped polycarbonate used, than observed with the aforementioned prior art stabilizers. A low loading of less than or equal to 5 mmol/Kg of the aryl carboxylate end-group in the thermoplastic composition can accomplish this. Such low loadings of substituted aromatic composition can allow the preparation of thermoplastic compositions with low color (i.e., without added pigment or dye) useful for making articles wherein the article having a thickness of 3.2±0.12 millimeters may have a light transmission of greater than 95% according to ASTM D1003-00, and wherein these properties are maintained after gamma irradiation at a total dose of up to about 81 kGy.

Advantageously, the aryl carboxylate end-capped polycarbonate is a polymer. Use of polymeric compounds as stabilizers for reducing yellowing can provide more uniform mixing and blending of the additive in higher quantities (typically greater than or equal to about 10 w % of the combined weights of polycarbonate that is not aryl carboxylate end-capped, and aryl carboxylate end-capped polycarbonate). In addition, in an embodiment, the aryl carboxylate end-capped polycarbonate may desirably be prepared at low cost by adding a suitable aryl carboxylic acid halide to a reaction, under suitable conditions, to prepare a polycarbonate.

Without wishing to be bound by theory, it is believed that the aryl carboxylate end-capped polycarbonates disclosed herein generate active radical species more efficiently than aromatic carbonate end-capped polycarbonates, and thereby provide a higher concentration of active radicals per unit of gamma radiation energy absorbed. Under this theory, these active radicals are believed to neutralize reactive species generated from polycarbonates, which would otherwise lead to polycarbonate degradation products that can lead to increased yellowness in the polycarbonate. Other additives which may enhance the resistance to yellowing may be included in the compositions. For example, including an ionizing radiation stabilizing additive, for example an aliphatic diol, with the polycarbonate that is not aryl carboxylate end-capped, and aryl carboxylate end-capped polycarbonate, can provide an additional synergistic improvement in resistance to increase in yellowness. However, where it is desirable to enhance the resistance to yellowing by including an additive, screening such additives is useful. For example, it has been found that including a hydrolysis stabilizer having epoxy functional groups with the polycarbonate, aryl carboxylate end-capped polycarbonate, and ionizing radiation stabilizing additive, can substantially adversely affect the ability of the polycarbonate to resist yellowing. It is believed that such epoxide compounds may quench the active yellowness inhibiting species generated by irradiation of the aryl carboxylate end-groups, thus increasing the yellowness of an article comprising the thermoplastic composition after gamma radiation exposure. Therefore, the amounts and identities of the polycarbonate, aryl carboxylate end-capped polycarbonate, and where also included, ionizing radiation stabilizing additive, are selected such that the increase in the yellowness of an article molded from the thermoplastic composition prepared therewith is minimized after gamma radiation exposure.

The increase in yellowness of a thermoplastic composition after gamma radiation exposure may be determined by measuring the yellowness index (YI) of a molded article prepared from the thermoplastic composition, and comparing to the YI of the article before exposure. The YI of the thermoplastic composition can be measured using transmittance and/or reflective spectroscopic methods depending upon the combination of transparency, color, and surface finish appearance of the article molded from the thermoplastic composition. Where a molded article prepared from the thermoplastic composition is either transparent or translucent; is colorless, white, or off-white; and is glossy, semi-glossy, or non-glossy, the YI of the molded article may be determined according to ASTM D1925-70. Where the molded article is opaque; is off-white or non-white; and has a glossy surface finish, the YI may be determined using reflectance measurement according to ASTM E313-73. Generally, higher doses of ionizing radiation give larger increases in measured yellowness index, and lower doses of ionizing radiation give smaller increases in yellowness index. It has been observed that the increase in measured yellowness index in the thermoplastic compositions does not necessarily increase linearly with increasing dose. The thermoplastic composition from which the article for testing is molded can contain additives including ionizing radiation stabilizing additives, and other additives typically included with polycarbonates, such as mold release agents and antioxidants, wherein the presence of these additives in an amount effective to perform the intended function does not significantly adversely affect the desired properties of the thermoplastic composition. Typically the total amount of these additives is less than or equal to 1.0 percent by weight of the total weight of components present in thermoplastic composition. In an exemplary embodiment, additives present in the thermoplastic composition used to prepare a molded article for yellowness testing may include 0.15 weight percent of 2-methyl-2,4-pentanediol as aliphatic diol, 0.27 weight percent pentaerythritol tetrastearate as a mold release agent, and 0.027 weight percent of 2,6-di-tert-butylphenyl) phosphite as antioxidant.

Thus, in an embodiment, a molded article having a thickness of 3.2±0.12 millimeters and consisting of the aryl carboxylate end-capped polycarbonate, the polycarbonate, and less than or equal to 1.0 percent total weight of aliphatic diol, a mold-release agent, and an antioxidant has, after exposure to a total gamma radiation dose of 81 kGy and when measured according to ASTM D1925-70, an increase in yellowness index (dYI) of less than or equal to 24.5, specifically less than or equal to 24, more specifically less than or equal to 23, and still more specifically less than or equal to 22, when compared to the unexposed article.

In another embodiment, a molded article having a thickness of 3.2±0.12 millimeters and consisting of the aryl carboxylate end-capped polycarbonate, the polycarbonate, and less than or equal to 1.0 percent total weight of aliphatic diol, a mold-release agent, and an antioxidant has, after exposure to a total gamma radiation dose of 59 kGy and when measured according to ASTM D1925-70, an increase in yellowness index (dYI) of less than or equal to 15.5, specifically less than or equal to 15.0, more specifically less than or equal to 14.0, and still more specifically less than or equal to 13.5, when compared to the unexposed article.

In another embodiment, a molded article having a thickness of 3.2±0.12 millimeters and consisting of the aryl carboxylate end-capped polycarbonate, the polycarbonate, and less than or equal to 1.0 percent total weight of aliphatic diol, a mold-release agent, and an antioxidant has, after exposure to a total gamma radiation dose of 30 kGy and when measured according to ASTM D1925-70, an increase in yellowness index (dYI) of less than or equal to 7.7, specifically less than or equal to 7.5, more specifically less than or equal to 7.3, and still more specifically less than or equal to 7.2, when compared to the unexposed article.

In addition to the polycarbonate, other resins, aryl carboxylate end-capped polycarbonate, and where desired, ionizing radiation stabilizing additive, the thermoplastic composition may include various other additives ordinarily incorporated with thermoplastic compositions of this type, with the proviso that an additive is selected such that it does not significantly adversely affect the dYI of the thermoplastic composition after treatment with an ionizing radiation. Mixtures of additives may be used. Such additives may be mixed at a suitable time during the mixing of the components for forming the thermoplastic composition.

The thermoplastic composition may comprise a colorant such as a pigment and/or dye additive. Suitable pigments include for example, inorganic pigments such as metal oxides and mixed metal oxides such as zinc oxide, titanium dioxides, iron oxides or the like; sulfides such as zinc sulfides, or the like; aluminates; sodium sulfo-silicates, sulfates, chromates, or the like; carbon blacks; zinc ferrites; ultramarine blue; Pigment Brown 24; Pigment Red 101; Pigment Yellow 119; organic pigments such as azos, di-azos, quinacridones, perylenes, naphthalene tetracarboxylic acids, flavanthrones, isoindolinones, tetrachloroisoindolinones, anthraquinones, anthanthrones, dioxazines, phthalocyanines, and azo lakes; Pigment Blue 60, Pigment Red 122, Pigment Red 149, Pigment Red 177, Pigment Red 179, Pigment Red 202, Pigment Violet 29, Pigment Blue 15, Pigment Blue 15:4, Pigment Blue 28, Pigment Green 7, Pigment Yellow 147 and Pigment Yellow 150, or combinations comprising at least one of the foregoing pigments. Pigments can be used in amounts of 0.01 to 10 percent by weight, based on the total weight of the polycarbonate that is not aryl carboxylate end-capped, and aryl carboxylate end-capped polycarbonate.

Suitable dyes can be organic materials and include, for example, coumarin dyes such as coumarin 460 (blue), coumarin 6 (green), nile red or the like; lanthanide complexes; hydrocarbon and substituted hydrocarbon dyes; polycyclic aromatic hydrocarbon dyes; scintillation dyes such as oxazole or oxadiazole dyes; aryl- or heteroaryl-substituted poly ($C_{2-8}$) olefin dyes; carbocyanine dyes; indanthrone dyes; phthalocyanine dyes; oxazine dyes; carbostyryl dyes; napthalenetetracarboxylic acid dyes; porphyrin dyes; bis(styryl)biphenyl dyes; acridine dyes; anthraquinone dyes; cyanine dyes; methine dyes; arylmethane dyes; azo dyes; indigoid dyes, thioindigoid dyes, diazonium dyes; nitro dyes; quinone imine dyes; aminoketone dyes; tetrazolium dyes; thiazole dyes; perylene dyes, perinone dyes; bis-benzoxazolylthiophene (BBOT); triarylmethane dyes; xanthene dyes; thioxanthene dyes; naphthalimide dyes; lactone dyes; fluorophores such as anti- stokes shift dyes which absorb in the near infrared wavelength and emit in the visible wavelength, or the like; luminescent dyes such as 7-amino-4-methylcoumarin; 3-(2'-benzothiazolyl)-7-diethylaminocoumarin; 2-(4-biphenylyl)-5-(4-t-butylphenyl)-1,3,4-oxadiazole; 2,5-bis-(4-biphenylyl)-oxazole; 2,2'-dimethyl-p-quaterphenyl; 2,2-dimethyl-p-terphenyl; 3,5,3'''', 5''''-tetra-t-butyl-p-quinquephenyl; 2,5-diphenylfuran; 2,5-diphenyloxazole; 4,4'-diphenylstilbene; 4-dicyanomethylene-2-methyl-6-(p-dimethylaminostyryl)-4H -pyran; 1,1'-diethyl-2,2'-carbocyanine iodide; 3,3'-diethyl-4,4', 5,5'-dibenzothiatricarbocyanine iodide; 7-dimethylamino-1-methyl-4-methoxy-8-azaquinolone-2; 7-dimethylamino-4-methylquinolone-2; 2-(4-(4-dimethylaminophenyl)-1,3-butadienyl)-3-ethylbenzothiazolium perchlorate; 3-diethylamino-7-diethyliminophenoxazonium perchlorate; 2-(1-naphthyl)-5-phenyloxazole; 2,2'-p-phenylen-bis(5-phenyloxazole); rhodamine 700; rhodamine 800; pyrene; chrysene; rubrene; coronene, or the like, or combinations comprising at least one of the foregoing dyes. Where it is desirable to use organic dyes and pigments, the dyes may be screened to determine their sensitivity to gamma radiation at a given exposure dose or range of exposure doses. Dyes can be used in amounts of 0.01 to 10 percent by weight, based on the total weight of the polycarbonate that is not aryl carboxylate end-capped, and aryl carboxylate end-capped polycarbonate.

The thermoplastic composition may include an impact modifier to increase its impact resistance, where the impact modifier is present in an amount that does not adversely affect the desired properties of the thermoplastic composition. These impact modifiers include elastomer-modified graft copolymers comprising (i) an elastomeric (i.e., rubbery) polymer substrate having a Tg less than 10° C., more specifically less than −10° C., or more specifically −40 to −80° C., and (ii) a rigid polymeric superstrate grafted to the elastomeric polymer substrate. As is known, elastomer-modified graft copolymers may be prepared by first providing the elastomeric polymer, then polymerizing the constituent monomer (s) of the rigid phase in the presence of the elastomer to obtain the graft copolymer. The grafts may be attached as graft branches or as shells to an elastomer core. The shell may merely physically encapsulate the core, or the shell may be partially or essentially completely grafted to the core.

Suitable materials for use as the elastomer phase include, for example, conjugated diene rubbers; copolymers of a conjugated diene with less than 50 wt % of a copolymerizable monomer; olefin rubbers such as ethylene propylene copolymers (EPR) or ethylene-propylene-diene monomer rubbers (EPDM); ethylene-vinyl acetate rubbers; silicone rubbers; elastomeric $C_{1-8}$ alkyl (meth)acrylates; elastomeric copolymers of $C_{1-8}$ alkyl (meth)acrylates with butadiene and/or styrene; or combinations comprising at least one of the foregoing elastomers.

Suitable conjugated diene monomers for preparing the elastomer phase are of formula (21):

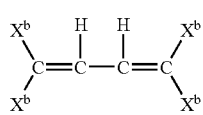

(21)

wherein each $X^b$ is independently hydrogen, $C_1$-$C_5$ alkyl, or the like. Examples of conjugated diene monomers that may be used are butadiene, isoprene, 1,3-heptadiene, methyl-1,3-pentadiene, 2,3-dimethyl-1,3-butadiene, 2-ethyl-1,3-pentadiene; 1,3- and 2,4-hexadienes, and the like, as well as mixtures comprising at least one of the foregoing conjugated diene monomers. Specific conjugated diene homopolymers include polybutadiene and polyisoprene.

Copolymers of a conjugated diene rubber may also be used, for example those produced by aqueous radical emulsion polymerization of a conjugated diene and one or more monomers copolymerizable therewith. Vinyl aromatic compounds may be copolymerized with the ethylenically unsaturated nitrile monomer to form a copolymer, wherein the vinylaromatic compounds can include monomers of formula (22):

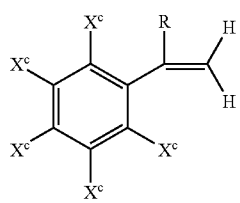

(22)

wherein each $X^c$ is independently hydrogen, $C_1$-$C_{12}$ alkyl, $C_3$-$C_{12}$ cycloalkyl, $C_6$-$C_{12}$ aryl, $C_7$-$C_{12}$ arylalkyl, $C_7$-$C_{12}$ alkylaryl, $C_1$-$C_{12}$ alkoxy, $C_3$-$C_{12}$ cycloalkoxy, $C_6$-$C_{12}$ aryloxy, chloro, bromo, or hydroxy, and R is hydrogen, $C_1$-$C_5$ alkyl, bromo, or chloro. Examples of suitable monovinylaromatic monomers that may be used include styrene, 3-methylstyrene, 3,5-diethylstyrene, 4-n-propylstyrene, alpha-methylstyrene, alpha-methyl vinyltoluene, alpha-chlorostyrene, alpha-bromostyrene, dichlorostyrene, dibromostyrene, tetrachlorostyrene, and the like, and combinations comprising at least one of the foregoing compounds. Styrene and/or alpha-methylstyrene may be used as monomers copolymerizable with the conjugated diene monomer.

Other monomers that may be copolymerized with the conjugated diene are monovinylic monomers such as itaconic acid, acrylamide, N-substituted acrylamide or methacrylamide, maleic anhydride, maleimide, N-alkyl-, aryl-, or haloaryl-substituted maleimide, glycidyl (meth)acrylates, and monomers of the generic formula (23):

(23)

wherein R is hydrogen, $C_1$-$C_5$ alkyl, bromo, or chloro, and $X^c$ is $C_1$-$C_{12}$ alkoxycarbonyl, $C_1$-$C_{12}$ aryloxycarbonyl, hydroxy carbonyl, or the like. Examples of monomers of formula (21) include, acrylic acid, methyl (meth)acrylate, ethyl (meth)acrylate, n-butyl (meth)acrylate, t-butyl (meth)acrylate, n-propyl (meth)acrylate, isopropyl (meth)acrylate, 2-ethylhexyl (meth)acrylate, and the like, and combinations comprising at least one of the foregoing monomers. Monomers such as n-butyl acrylate, ethyl acrylate, and 2-ethylhexyl acrylate are commonly used as monomers copolymerizable with the conjugated diene monomer. Mixtures of the foregoing monovinyl monomers and monovinylaromatic monomers may also be used.

Suitable (meth)acrylate monomers suitable for use as the elastomeric phase may be cross-linked, particulate emulsion homopolymers or copolymers of $C_{1-8}$ alkyl (meth)acrylates, in particular $C_{4-6}$ alkyl acrylates, for example n-butyl acrylate, t-butyl acrylate, n-propyl acrylate, isopropyl acrylate, 2-ethylhexyl acrylate, and the like, and combinations comprising at least one of the foregoing monomers. The $C_{1-8}$ alkyl (meth)acrylate monomers may optionally be polymerized in admixture with up to 15 wt % of comonomers of formulas (21), (22), or (23). Exemplary comonomers include but are not limited to butadiene, isoprene, styrene, methyl methacrylate, phenyl methacrylate, penethylmethacrylate, N-cyclohexylacrylamide, vinyl methyl ether, and mixtures comprising at least one of the foregoing comonomers. Optionally, up to 5 wt % a polyfunctional crosslinking comonomer may be present, for example divinylbenzene, alkylenediol di(meth)acrylates such as glycol bisacrylate, alkylenetriol tri(meth)acrylates, polyester di(meth)acrylates, bisacrylamides, triallyl cyanurate, triallyl isocyanurate, allyl (meth)acrylate, diallyl maleate, diallyl fumarate, diallyl adipate, triallyl esters of citric acid, triallyl esters of phosphoric acid, and the like, as well as combinations comprising at least one of the foregoing crosslinking agents.

The elastomer phase may be polymerized by mass, emulsion, suspension, solution or combined processes such as bulk-suspension, emulsion-bulk, bulk-solution or other techniques, using continuous, semibatch, or batch processes. The particle size of the elastomer substrate is not critical. For example, an average particle size of 0.001 to 25 micrometers, specifically 0.01 to 15 micrometers, or even more specifically 0.1 to 8 micrometers may be used for emulsion based polymerized rubber lattices. A particle size of 0.5 to 10 micrometers, specifically 0.6 to 1.5 micrometers may be used for bulk polymerized rubber substrates. Particle size may be measured by simple light transmittance methods or capillary hydrodynamic chromatography (CHDF). The elastomer phase may be a particulate, moderately cross-linked conjugated butadiene or $C_{4-6}$ alkyl acrylate rubber, and preferably has a gel content greater than 70 wt %. Also suitable are mixtures of butadiene with styrene and/or $C_{4-6}$ alkyl acrylate rubbers.

The elastomeric phase may provide 5 to 95 wt % of the total graft copolymer, more specifically 20 to 90 wt %, and even more specifically 40 to 85 wt % of the elastomer-modified graft copolymer, the remainder being the rigid graft phase.

The rigid phase of the elastomer-modified graft copolymer may be formed by graft polymerization of a mixture comprising a monovinylaromatic monomer and optionally one or more comonomers in the presence of one or more elastomeric polymer substrates. The above-described monovinylaromatic monomers of formula (22) may be used in the rigid graft phase, including styrene, alpha-methyl styrene, halostyrenes such as dibromostyrene, vinyltoluene, vinylxylene, butylstyrene, para-hydroxystyrene, methoxystyrene, or the like, or combinations comprising at least one of the foregoing monovinylaromatic monomers. Suitable comonomers include, for example, the above-described monovinylic monomers and/or monomers of the general formula (23). In one embodiment, R is hydrogen or $C_1$-$C_2$ alkyl, and $X^e$ is cyano or $C_1$-$C_{12}$ alkoxycarbonyl. Specific examples of suitable comonomers for use in the rigid phase include, methyl (meth)acrylate, ethyl (meth)acrylate, n-propyl (meth)acrylate, isopropyl (meth)acrylate, and the like, and combinations comprising at least one of the foregoing comonomers.

The relative ratio of monovinylaromatic monomer and comonomer in the rigid graft phase may vary widely depending on the type of elastomer substrate, type of monovinylaromatic monomer(s), type of comonomer(s), and the desired properties of the impact modifier. The rigid phase may generally comprise up to 100 wt % of monovinyl aromatic monomer, specifically 30 to 100 wt %, more specifically 50 to 90 wt % monovinylaromatic monomer, with the balance being comonomer(s).

Depending on the amount of elastomer-modified polymer present, a separate matrix or continuous phase of ungrafted rigid polymer or copolymer may be simultaneously obtained along with the elastomer-modified graft copolymer. Typically, such impact modifiers comprise 40 to 95 wt % elastomer-modified graft copolymer and 5 to 65 wt % graft copolymer, based on the total weight of the impact modifier. In another embodiment, such impact modifiers comprise 50 to 85 wt %, more specifically 75 to 85 wt % rubber-modified graft copolymer, together with 15 to 50 wt %, more specifically 15 to 25 wt % graft copolymer, based on the total weight of the impact modifier.

Another specific type of elastomer-modified impact modifier comprises structural units derived from at least one silicone rubber monomer, a branched acrylate rubber monomer having the formula $H_2C=C(R^d)C(O)OCH_2CH_2R^e$, wherein $R^d$ is hydrogen or a $C_1$-$C_8$ linear or branched alkyl group and $R^e$ is a branched $C_3$-$C_{16}$ alkyl group; a first graft link monomer; a polymerizable alkenyl-containing organic material; and a second graft link monomer. The silicone rubber monomer may comprise, for example, a cyclic siloxane, tetraalkoxysilane, trialkoxysilane, (acryloxy)alkoxysilane, (mercaptoalkyl)alkoxysilane, vinylalkoxysilane, or allylalkoxysilane, alone or in combination, e.g., decamethylcyclopentasiloxane, dodecamethylcyclohexasiloxane, trimethyltriphenylcyclotrisiloxane, tetramethyltetraphenylcyclotetrasiloxane, tetramethyltetravinylcyclotetrasiloxane, octaphenylcyclotetrasiloxane., octamethylcyclotetrasiloxane and/or tetraethoxysilane.

Exemplary branched acrylate rubber monomers include iso-octyl acrylate, 6-methyloctyl acrylate, 7-methyloctyl acrylate, 6-methylheptyl acrylate, and the like, alone or in combination. The polymerizable, alkenyl-containing organic material may be, for example, a monomer of formula (22) or (23), e.g., styrene, alpha-methylstyrene, or an unbranched (meth)acrylate such as methyl methacrylate, 2-ethylhexyl methacrylate, methyl acrylate, ethyl acrylate, n-propyl acrylate, or the like, alone or in combination.

The at least one first graft link monomer may be an (acryloxy)alkoxysilane, a (mercaptoalkyl)alkoxysilane, a vinylalkoxysilane, or an allylalkoxysilane, alone or in combination, e.g., (gamma-methacryloxypropyl) (dimethoxy)methylsilane and/or (3-mercaptopropyl) trimethoxysilane. The at least one second graft link monomer is a polyethylenically unsaturated compound having at least one allyl group, such as allyl methacrylate, triallyl cyanurate, or triallyl isocyanurate, alone or in combination.

The silicone-acrylate impact modifier compositions can be prepared by emulsion polymerization, wherein, for example at least one silicone rubber monomer is reacted with at least one first graft link monomer at a temperature from 30° C. to 110° C. to form a silicone rubber latex, in the presence of a surfactant such as dodecylbenzenecarboxylic acid. Alternatively, a cyclic siloxane such as cyclooctamethyltetrasiloxane and tetraethoxyorthosilicate may be reacted with a first graft link monomer such as (gamma-methacryloxypropyl) methyldimethoxysilane, to afford silicone rubber having an average particle size from 100 nanometers to 2 micrometers. At least one branched acrylate rubber monomer is then polymerized with the silicone rubber particles, optionally in presence of a cross linking monomer, such as allylmethacrylate in the presence of a free radical generating polymerization catalyst such as benzoyl peroxide. This latex is then reacted with a polymerizable alkenyl-containing organic material and a second graft link monomer. The latex particles of the graft silicone-acrylate rubber hybrid may be separated from the aqueous phase through coagulation (by treatment with a coagulant) and dried to a fine powder to produce the silicone-acrylate rubber impact modifier composition. This method can be generally used for producing the silicone-acrylate impact modifier having a particle size from 100 nanometers to 2 micrometers.

Processes known for the formation of the foregoing elastomer-modified graft copolymers include mass, emulsion, suspension, and solution processes, or combined processes such as bulk-suspension, emulsion-bulk, bulk-solution or other techniques, using continuous, semibatch, or batch processes.

The foregoing types of impact modifiers, including SAN copolymers, can be prepared by an emulsion polymerization process that is free of basic materials such as alkali metal salts of $C_{6-30}$ fatty acids, for example sodium stearate, lithium stearate, sodium oleate, potassium oleate, and the like; alkali metal carbonates, amines such as dodecyl dimethyl amine, dodecyl amine, and the like; and ammonium salts of amines. Such materials are commonly used as surfactants in emulsion polymerization, and may catalyze transesterification and/or degradation of polycarbonates. Instead, ionic sulfate, sulfonate or phosphate surfactants may be used in preparing the impact modifiers, particularly the elastomeric substrate portion of the impact modifiers. Suitable surfactants include, for example, $C_{1-22}$ alkyl or $C_{7-25}$ alkylaryl sulfonates, $C_{1-22}$ alkyl or $C_{7-25}$ alkylaryl sulfates, $C_{1-22}$ alkyl or $C_{7-25}$ alkylaryl phosphates, substituted silicates, and mixtures thereof. A specific surfactant is a $C_{6-16}$, specifically a $C_{8-12}$ alkyl sulfonate. In the practice, any of the above-described impact modifiers may be used providing it is free of the alkali metal salts of fatty acids, alkali metal carbonates and other basic materials.

A specific impact modifier of this type is a methyl methacrylate-butadiene-styrene (MBS) impact modifier wherein the butadiene substrate is prepared using above-described sulfonates, sulfates, or phosphates as surfactants. Other examples of elastomer-modified graft copolymers besides ABS and MBS include but are not limited to acrylonitrile-styrene-butyl acrylate (ASA), methyl methacrylate-acrylonitrile-butadiene-styrene (MABS), and acrylonitrile-ethylene-propylene-diene-styrene (AES). When present, impact modifiers can be present in the thermoplastic composition in amounts of 0.1 to 30 percent by weight, based on the total weight of the polycarbonate that is not aryl carboxylate end-capped, and aryl carboxylate end-capped polycarbonate.

The thermoplastic composition may include fillers or reinforcing agents. The fillers and reinforcing agents may desirably be in the form of nanoparticles, i.e., particles with a median particle size ($D_{50}$) smaller than 100 nm as determined using light scattering methods. Where used, suitable fillers or reinforcing agents include, for example, silicates and silica powders such as aluminum silicate (mullite), synthetic calcium silicate, zirconium silicate, fused silica, crystalline silica graphite, natural silica sand, or the like; boron powders such as boron-nitride powder, boron-silicate powders, or the like; oxides such as $TiO_2$, aluminum oxide, magnesium oxide, or the like; calcium sulfate (as its anhydride, dihydrate or trihydrate); calcium carbonates such as chalk, limestone, marble, synthetic precipitated calcium carbonates, or the like; talc, including fibrous, modular, needle shaped, lamellar talc, or the like; wollastonite; surface-treated wollastonite; glass spheres such as hollow and solid glass spheres, silicate spheres, cenospheres, aluminosilicate (armospheres), or the like; kaolin, including hard kaolin, soft kaolin, calcined kaolin, kaolin comprising various coatings known in the art to facilitate compatibility with the polymeric matrix resin, or the like; single crystal fibers or "whiskers" such as silicon carbide, alumina, boron carbide, iron, nickel, copper, or the like; fibers (including continuous and chopped fibers) such as asbestos, carbon fibers, glass fibers, such as E, A, C, ECR, R, S, D, or NE glasses, or the like; sulfides such as molybdenum sulfide, zinc sulfide or the like; barium compounds such as barium titanate, barium ferrite, barium sulfate, heavy spar, or the like; metals and metal oxides such as particulate or fibrous aluminum, bronze, zinc, copper and nickel or the like; flaked fillers such as glass flakes, flaked silicon carbide, aluminum diboride, aluminum flakes, steel flakes or the like; fibrous fillers, for example short inorganic fibers such as those derived from blends comprising at least one of aluminum silicates, aluminum oxides, magnesium oxides, and calcium sulfate hemihydrate or the like; natural fillers and reinforcements, such as wood flour obtained by pulverizing wood, fibrous products such as cellulose, cotton, sisal, jute, starch, cork flour, lignin, ground nut shells, corn, rice grain husks or the like; organic fillers such as polytetrafluoroethylene; reinforcing organic fibrous fillers formed from organic polymers capable of forming fibers such as poly(ether ketone), polyimide, polybenzoxazole, poly(phenylene sulfide), polyesters, polyethylene, aromatic polyamides, aromatic polyimides, polyetherimides, polytetrafluoroethylene, acrylic resins, poly(vinyl alcohol) or the like; as well as additional fillers and reinforcing agents such as mica, clay, feldspar, flue dust, fillite, quartz, quartzite, perlite, tripoli, diatomaceous earth, carbon black, or the like, or combinations comprising at least one of the foregoing fillers or reinforcing agents.

The fillers and reinforcing agents may be coated with a layer of metallic material to facilitate conductivity, or surface treated with silanes to improve adhesion and dispersion with the polymeric matrix resin. In addition, the reinforcing fillers may be provided in the form of monofilament or multifilament fibers and may be used either alone or in combination with other types of fiber, through, for example, co-weaving or core/sheath, side-by-side, orange-type or matrix and fibril constructions, or by other methods known to one skilled in the art of fiber manufacture. Suitable cowoven structures include, for example, glass fiber-carbon fiber, carbon fiber-aromatic polyimide (aramid) fiber, and aromatic polyimide fiberglass fiber or the like. Fibrous fillers may be supplied in the form of, for example, rovings, woven fibrous reinforcements, such as 0-90 degree fabrics or the like; non-woven fibrous reinforcements such as continuous strand mat, chopped strand mat, tissues, papers and felts or the like; or three-dimensional reinforcements such as braids. Fillers can be used in amounts of 0 to 90 percent by weight, based on the total weight of the polycarbonate that is not aryl carboxylate end-capped, and aryl carboxylate end-capped polycarbonate.

Suitable antioxidant additives include, for example, organophosphites such as tris(nonyl phenyl)phosphite, tris(2,4-di-t-butylphenyl)phosphite, bis(2,4-di-t-butylphenyl)pentaerythritol diphosphite, distearyl pentaerythritol diphosphite or the like; alkylated monophenols or polyphenols; alkylated reaction products of polyphenols with dienes, such as tetrakis[methylene(3,5-di-tert-butyl-4-hydroxyhydrocinnamate)] methane, or the like; butylated reaction products of para-cresol or dicyclopentadiene; alkylated hydroquinones; hydroxylated thiodiphenyl ethers; alkylidene-bisphenols; benzyl compounds; esters of beta-(3,5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds such as distearylthiopropionate, dilaurylthiopropionate, ditridecylthiodipropionate, octadecyl-3-(3,5-di-tert-butyl-4-hydroxyphenyl)propionate, pentaerythrityl-tetrakis[3-(3,5-di-tert-butyl-4-hydroxyphenyl)propionate or the like; amides of beta-(3,5-di-tert-butyl-4-hydroxyphenyl)-propionic acid or the like, or combinations comprising at least one of the foregoing antioxidants. Antioxidants can be used in amounts of 0.0001 to 1 percent by weight, based on the total weight of the polycarbonate that is not aryl carboxylate end-capped, and aryl carboxylate end-capped polycarbonate.

Suitable heat stabilizer additives include, for example, organophosphites such as triphenyl phosphite, tris-(2,6-dimethylphenyl)phosphite, tris-(mixed mono-and di-nonylphenyl)phosphite or the like; phosphonates such as dimethylbenzene phosphonate or the like, phosphates such as trimethyl phosphate, or the like, or combinations comprising at least one of the foregoing heat stabilizers. Heat stabilizers can be used in amounts of 0.0001 to 1 percent by weight, based on the total weight of the polycarbonate that is not aryl carboxylate end-capped, and aryl carboxylate end-capped polycarbonate.

Light stabilizers and/or ultraviolet light (UV) absorbing additives may also be used. Suitable light stabilizer additives include, for example, benzotriazoles such as 2-(2-hydroxy-5-methylphenyl)benzotriazole, 2-(2-hydroxy-5-tert-octylphenyl)-benzotriazole and 2-hydroxy-4-n-octoxy benzophenone, or the like, or combinations comprising at least one of the foregoing light stabilizers. Light stabilizers can be used in amounts of 0.0001 to 1 percent by weight, based on the total weight of the polycarbonate that is not aryl carboxylate end-capped, and aryl carboxylate end-capped polycarbonate.

Suitable UV absorbing additives include for example, hydroxybenzophenones; hydroxybenzotriazoles; hydroxybenzotriazines; cyanoacrylates; oxanilides; benzoxazinones; 2-(2H-benzotriazol-2-yl)-4-(1,1,3,3-tetramethylbutyl)-phenol (CYASORB® 5411); 2-hydroxy-4-n-octyloxybenzophenone (CYASORB® 531); 2-[4,6-bis(2,4-dimethylphenyl)-1,3,5-triazin-2-yl]-5-(octyloxy) -phenol (CYASORB® 1164); 2,2'-(1,4-phenylene)bis(4H-3,1-benzoxazin-4-one) (CYASORB® UV-3638); 1,3-bis[(2-cyano-3,3-diphenylacryloyl)oxy]-2,2-bis[[(2-cyano-3,3-diphenylacryloyl)oxy]methyl] propane (UVINUL® 3030); 2,2'-(1,4-phenylene) bis(4H-3,1-benzoxazin-4-one); 1,3-bis[(2-cyano-3,3-diphenylacryloyl)oxy]-2,2-bis[[(2-cyano-3,3- diphenylacryloyl)oxy]methyl] propane; nano-size inorganic materials such as titanium oxide, cerium oxide, and zinc oxide, all with particle size less than 100 nanometers; or the like, or combinations comprising at least one of the foregoing UV absorbers. UV absorbers can be used in amounts of 0.0001 to 1 percent by weight, based on the total weight of the polycarbonate that is not aryl carboxylate end-capped, and aryl carboxylate end-capped polycarbonate.

Plasticizers, lubricants, and/or mold release agents additives may also be used. There is considerable overlap among these types of materials, which include, for example, phthalic acid esters such as dioctyl-4,5-epoxy-hexahydrophthalate; tris-(octoxycarbonylethyl)isocyanurate; tristearin; di- or polyfunctional aromatic phosphates such as resorcinol tetraphenyl diphosphate (RDP), the bis(diphenyl) phosphate of hydroquinone and the bis(diphenyl) phosphate of bisphenol-A; poly-alpha-olefins; epoxidized soybean oil; silicones, including silicone oils; esters, for example, fatty acid esters such as alkyl stearyl esters, e.g., methyl stearate; stearyl stearate, pentaerythritol tetrastearate, and the like; mixtures of methyl stearate and hydrophilic and hydrophobic nonionic surfactants comprising polyethylene glycol polymers, polypropylene glycol polymers, and copolymers thereof, e.g., methyl stearate and polyethylene-polypropylene glycol copolymers in a suitable solvent; waxes such as beeswax, montan wax, paraffin wax or the like. Such materials can be used in amounts of 0.001 to 1 percent by weight, specifically 0.01 to 0.75 percent by weight, more specifically 0.1 to 0.5 percent by weight, based on the total weight of the polycarbonate that is not aryl carboxylate end-capped, and aryl carboxylate end-capped polycarbonate.

The term "antistatic agent" refers to monomeric, oligomeric, or polymeric materials that can be processed into polymer resins and/or sprayed onto materials or articles to improve conductive properties and overall physical performance. Examples of monomeric antistatic agents include glycerol monostearate, glycerol distearate, glycerol tristearate, ethoxylated amines, primary, secondary and tertiary amines, ethoxylated alcohols, alkyl sulfates, alkylarylsulfates, alkylphosphates, alkylaminesulfates, alkyl sulfonate salts such as sodium stearyl sulfonate, sodium dodecylbenzenesulfonate or the like, quaternary ammonium salts, quaternary ammonium resins, imidazoline derivatives, sorbitan esters, ethanolamides, betaines, or the like, or combinations comprising at least one of the foregoing monomeric antistatic agents.

Exemplary polymeric antistatic agents include certain polyesteramides polyether-polyamide (polyetheramide) block copolymers, polyetheresteramide block copolymers, polyetheresters, or polyurethanes, each containing polyalkylene glycol moieties polyalkylene oxide units such as polyethylene glycol, polypropylene glycol, polytetramethylene glycol, and the like. Such polymeric antistatic agents are commercially available, for example Pelestat® 6321 (Sanyo) or Pebax® MH1657 (Atofina), Irgastat® P18 and P22 (Ciba-Geigy). Other polymeric materials that may be used as antistatic agents are inherently conducting polymers such as polyaniline (commercially available as PANIPOL®EB from Panipol), polypyrrole and polythiophene (commercially available from Bayer), which retain some of their intrinsic conductivity after melt processing at elevated temperatures. In one embodiment, carbon fibers, carbon nanofibers, carbon nanotubes, carbon black, or any combination of the foregoing may be used in a polymeric resin containing chemical antistatic agents to render the composition electrostatically dissipative. Antistatic agents can be used in amounts of 0.0001 to 5 percent by weight, based on the total weight of the polycarbonate that is not aryl carboxylate end-capped, and aryl carboxylate end-capped polycarbonate.

Suitable flame retardant that may be added may be organic compounds that include phosphorus, bromine, and/or chlorine. Non-brominated and non-chlorinated phosphorus-containing flame retardants may be preferred in certain applications for regulatory reasons, for example organic phosphates and organic compounds containing phosphorus-nitrogen bonds.

One type of exemplary organic phosphate is an aromatic phosphate of the formula $(GO)_3P=O$, wherein each G is independently an alkyl, cycloalkyl, aryl, alkylaryl, or arylalkyl group, provided that at least one G is an aromatic group. Two of the G groups may be joined together to provide a cyclic group, for example, diphenyl pentaerythritol diphosphate. Other suitable aromatic phosphates may be, for example, phenyl bis(dodecyl) phosphate, phenyl bis(neopentyl) phosphate, phenyl bis(3,5,5'-trimethylhexyl) phosphate, ethyl diphenyl phosphate, 2-ethylhexyl di(p-tolyl) phosphate, bis(2-ethylhexyl) p-tolyl phosphate, tritolyl phosphate, bis(2-ethylhexyl) phenyl phosphate, tri(nonylphenyl) phosphate, bis(dodecyl) p-tolyl phosphate, dibutyl phenyl phosphate, 2-chloroethyl diphenyl phosphate, p-tolyl bis(2,5,5'-trimethylhexyl) phosphate, 2-ethylhexyl diphenyl phosphate, or the like. A specific aromatic phosphate is one in which each G is aromatic, for example, triphenyl phosphate, tricresyl phosphate, isopropylated triphenyl phosphate, and the like.

Di- or polyfunctional aromatic phosphorus-containing compounds are also useful, for example, compounds of the formulas below:

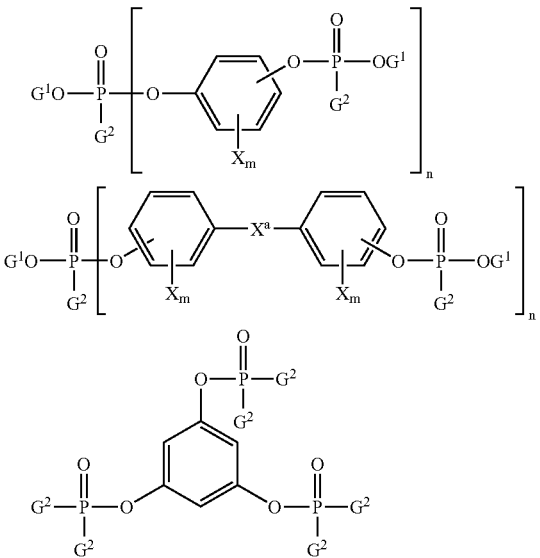

wherein each $G^1$ is independently a hydrocarbon having 1 to 30 carbon atoms; each $G^2$ is independently a hydrocarbon or hydrocarbonoxy having 1 to 30 carbon atoms; each $X^a$ is independently a hydrocarbon having 1 to 30 carbon atoms; each X is independently a bromine or chlorine; m is 0 to 4, and n is 1 to 30. Examples of suitable di- or polyfunctional aromatic phosphorus-containing compounds include resorcinol tetraphenyl diphosphate (RDP), the bis(diphenyl) phosphate of hydroquinone and the bis(diphenyl) phosphate of bisphenol-A, respectively, their oligomeric and polymeric counterparts, and the like.

Exemplary suitable flame retardant compounds containing phosphorus-nitrogen bonds include phosphonitrilic chloride, phosphorus ester amides, phosphoric acid amides, phosphonic acid amides, phosphinic acid amides, tris(aziridinyl) phosphine oxide. When present, phosphorus-containing flame retardants can be present in amounts of 0.1 to 10 percent by weight, based on the total weight of the polycarbonate that is not aryl carboxylate end-capped, and aryl carboxylate end-capped polycarbonate.

Halogenated materials may also be used as flame retardants, for example halogenated compounds and resins of formula (24):

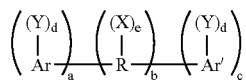

(24)

wherein R is an alkylene, alkylidene or cycloaliphatic linkage, e.g., methylene, ethylene, propylene, isopropylene, isopropylidene, butylene, isobutylene, amylene, cyclohexylene, cyclopentylidene, or the like; or an oxygen ether, carbonyl, amine, or a sulfur containing linkage, e.g., sulfide, sulfoxide, sulfone, or the like. R can also consist of two or more alkylene or alkylidene linkages connected by such groups as aromatic, amino, ether, carbonyl, sulfide, sulfoxide, sulfone, or the like.

Ar and Ar' in formula (24) are each independently mono- or polycarbocyclic aromatic groups such as phenylene, biphenylene, terphenylene, naphthylene, or the like.

Y is an organic, inorganic, or organometallic radical, for example: halogen, e.g., chlorine, bromine, iodine, fluorine; ether groups of the general formula OE, wherein E is a monovalent hydrocarbon radical similar to X; monovalent hydrocarbon groups of the type represented by R; or other substituents, e.g., nitro, cyano, and the like, said substituents being essentially inert provided that there is at least one and preferably two halogen atoms per aryl nucleus.

When present, each X is independently a monovalent hydrocarbon group, for example an alkyl group such as methyl, ethyl, propyl, isopropyl, butyl, decyl, or the like; an aryl groups such as phenyl, naphthyl, biphenyl, xylyl, tolyl, or the like; and arylalkyl group such as benzyl, ethylphenyl, or the like; a cycloaliphatic group such as cyclopentyl, cyclohexyl, or the like. The monovalent hydrocarbon group may itself contain inert substituents.

Each d is independently 1 to a maximum equivalent to the number of replaceable hydrogens substituted on the aromatic rings comprising Ar or Ar'. Each e is independently 0 to a maximum equivalent to the number of replaceable hydrogens on R. Each a, b, and c is independently a whole number, including 0. When b is not 0, neither a nor c may be 0. Otherwise either a or c, but not both, may be 0. Where b is 0, the aromatic groups are joined by a direct carbon-carbon bond.

The hydroxyl and Y substituents on the aromatic groups, Ar and Ar', can be varied in the ortho, meta or para positions on the aromatic rings and the groups can be in any possible geometric relationship with respect to one another.

Included within the scope of the above formula are bisphenols of which the following are representative: 2,2-bis-(3,5-dichlorophenyl)-propane; bis-(2-chlorophenyl)-methane; bis (2,6-dibromophenyl)-methane; 1,1-bis-(4-iodophenyl) -ethane; 1,2-bis-(2,6-dichlorophenyl)-ethane; 1,1-bis-(2-chloro-4-iodophenyl)ethane; 1,1-bis-(2-chloro-4-methylphenyl)-ethane; 1,1-bis-(3,5-dichlorophenyl)-ethane; 2,2-bis-(3-phenyl-4-bromophenyl)-ethane; 2,6-bis-(4,6-dichloronaphthyl)-propane; 2,2-bis-(2,6-dichlorophenyl)-pentane; 2,2-bis-(3,5-dibromophenyl)-hexane; bis-(4-chlorophenyl)-phenyl-methane; bis-(3,5-dichlorophenyl)-cyclohexylmethane; bis-(3-nitro-4-bromophenyl)-methane; bis-(4-hydroxy-2,6-dichloro-3-methoxyphenyl) -methane; and 2,2-bis-(3,5-dichloro-4-hydroxyphenyl)-propane 2,2 bis-(3-bromo-4-hydroxyphenyl)-propane. Also included within the above structural formula are: 1,3-dichlorobenzene, 1,4-dibromobenzene, 1,3-dichloro-4-hydroxybenzene, and biphenyls such as 2,2'-dichlorobiphenyl, polybrominated 1,4-diphenoxybenzene, 2,4'-dibromobiphenyl, and 2,4'-dichlorobiphenyl as well as decabromo diphenyl oxide, and the like.

Also useful are oligomeric and polymeric halogenated aromatic compounds, such as a copolycarbonate of bisphenol A and tetrabromobisphenol A and a carbonate precursor, e.g., phosgene. Metal synergists, e.g., antimony oxide, may also be used with the flame retardant. When present, halogen containing flame retardants can be present in amounts of 0.1 to 10 percent by weight, based on the total weight of the polycarbonate that is not aryl carboxylate end-capped, and aryl carboxylate end-capped polycarbonate.

Inorganic flame retardants may also be used, for example salts of $C_{2-16}$ alkyl sulfonate salts such as potassium perfluorobutane sulfonate (Rimar salt), potassium perfluoroctane sulfonate, tetraethylammonium perfluorohexane sulfonate, and potassium diphenylsulfone sulfonate, and the like; salts formed by reacting for example an alkali metal or alkaline earth metal (for example lithium, sodium, potassium, magnesium, calcium and barium salts) and an inorganic acid complex salt, for example, an oxo-anion, such as alkali metal and alkaline-earth metal salts of carbonic acid, such as $Na_2CO_3$, $K_2CO_3$, $MgCO_3$, $CaCO_3$, and $BaCO_3$ or fluoro-anion complexes such as $Li_3AlF_6$, $BaSiF_6$, $KBF_4$, $K_3AlF_6$, $KAlF_4$, $K_2SiF_6$, and/or $Na_3AlF_6$ or the like. When present, inorganic flame retardant salts can be present in amounts of 0.1 to 5 percent by weight, based on the total weight of the polycarbonate that is not aryl carboxylate end-capped, and aryl carboxylate end-capped polycarbonate.

Anti-drip agents may also be used, for example a fibril forming or non-fibril forming fluoropolymer such as polytetrafluoroethylene (PTFE). The anti-drip agent may be encapsulated by a rigid copolymer as described above, for example styrene-acrylonitrile copolymer (SAN). PTFE encapsulated in SAN is known as TSAN. Encapsulated fluoropolymers may be made by polymerizing the encapsulating polymer in the presence of the fluoropolymer, for example an aqueous dispersion. TSAN may provide significant advantages over PTFE, in that TSAN may be more readily dispersed in the composition. A suitable TSAN may comprise, for example, 50 wt % PTFE and 50 wt % SAN, based on the total weight of the encapsulated fluoropolymer. The SAN may comprise, for example, 75 wt % styrene and 25 wt % acrylonitrile based on the total weight of the copolymer. Alternatively, the fluoropolymer may be pre-blended in some manner with a second polymer, such as for, example, an aromatic polycarbonate resin or SAN to form an agglomerated material for use as an anti-drip agent. Either method may be used to produce an encapsulated fluoropolymer. Antidrip agents can be used in amounts of 0.1 to 5 percent by weight, based on the total weight of the polycarbonate that is not aryl carboxylate end-capped, and aryl carboxylate end-capped polycarbonate.

While it is contemplated that other resins may be used in the thermoplastic compositions described herein, the aryl carboxylate end-capped polycarbonates are particularly suited for use in thermoplastic compositions that contain only polycarbonate-type resins as described herein (homopolycarbonates, copolyester carbonates, and combinations thereof). Thus, in an embodiment, a thermoplastic composition consists essentially of a polycarbonate that is not aryl carboxylate end-capped, and an aryl carboxylate end capped polycarbonate. In another embodiment, the thermoplastic composition consists essentially of a polycarbonate that is not aryl carboxylate end-capped, and 0.01 to 500 millimoles per kilogram (mmol/Kg), more specifically 0.1 to 400 mmol/Kg, even more specifically 1 to 300 mmol/kg of an aryl carboxylate end-capped polycarbonate, based on the combined weight of the polycarbonate resin and the aryl carboxylate end-capped polycarbonate, excluding any other additives and/or fillers. In another embodiment, a thermoplastic composition consists essentially of a polycarbonate composition comprising 0 to 99.9 wt % of a polycarbonate that is not aryl carboxylate end-capped, and of 0.1 to 100 wt % of an aryl carboxylate end-capped polycarbonate. In another embodiment, a thermoplastic composition consists essentially of a polycarbonate composition comprising 20 to 99 wt % of a polycarbonate that is not aryl carboxylate end-capped, and 1 to 80 wt % of an aryl carboxylate end-capped polycarbonate. In another embodiment, a thermoplastic composition consists essentially of a polycarbonate composition comprising 50 to 98 wt % of a polycarbonate that is not aryl carboxylate end-capped, and 2 to 50 wt % of an aryl carboxylate end-capped polycarbonate. In still another embodiment, a thermoplastic composition consists essentially of a polycarbonate composition comprising 60 to 95 wt % of a polycarbonate that is not aryl carboxylate end-capped, and 5 to 40 wt % of an aryl carboxylate end-capped polycarbonate. In still another embodiment, a thermoplastic composition consists essentially of a polycarbonate composition comprising 70 to 91 wt % of a polycarbonate that is not aryl carboxylate end-capped, and 9 to 30 wt % of an aryl carboxylate end-capped polycarbonate. Each of the foregoing wt % values are based on the combined weights of the polycarbonate that is not aryl carboxylate end-capped, and the aryl carboxylate end-capped polycarbonate, wherein each of the foregoing weight percentages is based on the combined weight of the polycarbonate that is not aryl carboxylate end-capped, and the aryl carboxylate end-capped polycarbonate, excluding any other additives and/or fillers. In a further embodiment, the thermoplastic composition comprises 0.001 to 1 wt % of an ionizing radiation stabilizing compound, based on the combined weight of the polycarbonate that is not aryl carboxylate end-capped, and the aryl carboxylate end-capped polycarbonate.

In a further embodiment, the thermoplastic composition may comprise an additive selected from impact modifier, filler, antioxidant, heat stabilizer, light stabilizer, ultraviolet light absorber, plasticizer, mold release agent, lubricant, antistatic agent, pigment, dye, flame retardant, anti-drip agent, or a combination comprising at least one of these.

The thermoplastic composition may be manufactured by methods generally available in the art, for example, in one embodiment, in one manner of proceeding, powdered polycarbonate, aryl carboxylate end-capped polycarbonate, and other optional components including ionizing radiation stabilizing additive and/or other additives are first blended, in a HENSCHEL-Mixer® high speed mixer. Other low shear processes including but not limited to hand mixing may also accomplish this blending. The blend is then fed into the throat of an extruder via a hopper. Alternatively, one or more of the components may be incorporated into the composition by feeding directly into the extruder at the throat and/or downstream through a sidestuffer. Where desired, the aryl carboxylate end-capped polycarbonate that is not aryl carboxylate end-capped, and any desired polymer and/or additives may also be compounded into a masterbatch and combined with a desired polymeric resin and fed into the extruder. The extruder is generally operated at a temperature higher than that necessary to cause the composition to flow. The extrudate is immediately quenched in a water batch and pelletized. The pellets, so prepared, when cutting the extrudate may be one-fourth inch long or less as desired. Such pellets may be used for subsequent molding, shaping, or forming.

In a specific embodiment, a method of preparing a thermoplastic composition comprises melt combining a polycarbonate that is not aryl carboxylate end-capped, and an aryl carboxylate end-capped polycarbonate. The melt combining can be done by extrusion. In an embodiment, the proportions of polycarbonate that is not aryl carboxylate end-capped, and aryl carboxylate end-capped polycarbonate are selected such that the optical properties of the thermoplastic composition are maximized while mechanical performance is at a desirable level. In a further specific embodiment, an ionizing radiation stabilizing additive is combined with the polycarbonate that is not aryl carboxylate end-capped, and aryl carboxylate end-capped polycarbonate to make the thermoplastic composition. In an embodiment, the proportions of polycarbonate, aryl carboxylate end-capped polycarbonate, and where desired, ionizing radiation stabilizing additive, are selected such that the optical properties of the thermoplastic composition are maximized while mechanical performance is at a desirable level.

In a specific embodiment, the extruder is a twin-screw extruder. The extruder is typically operated at a temperature of 180 to 385° C., specifically 200 to 330° C., more specifically 220 to 300° C., wherein the die temperature may be different. The extruded thermoplastic composition is quenched in water and pelletized.

Shaped, formed, or molded articles comprising the thermoplastic compositions are also provided. The thermoplastic compositions may be molded into useful shaped articles by a variety of means such as injection molding, extrusion, rotational molding, blow molding and thermoforming. In a specific embodiment, molding is done by injection molding. Desirably, the thermoplastic composition has excellent mold filling capability and is useful to form articles such as, for example, bottles, syringes, dialysis fittings, tubing, sample vials, blood bags, petri dishes, beakers, centrifuge tubes, spatulas, connectors, trocars, stopcocks, luer locks, Y-sites, catheters, oxygenator housings, trays, dental instruments, pipettes, glucose meters, inhalers, and the like.

In an embodiment, a method of sterilizing an article comprising the thermoplastic composition comprising the aryl carboxylate end-capped polycarbonate comprises irradiating the article with an ionizing radiation. In a specific embodiment, the ionizing radiation is gamma radiation. In a further specific embodiment, the article is irradiated with a dose of gamma rays of about 10 to about 85 kGy. The article, prepared with the thermoplastic composition comprising aryl carboxylate end-capped polycarbonate and so irradiated shows a less increase in dYI than the comparable article prepared without aryl carboxylate end-capped polycarbonate.

The thermoplastic composition is further illustrated by the following non-limiting examples.

All thermoplastic compositions were compounded on a Werner & Pfleiderer co-rotating twin screw extruder (Length/Diameter (L/D) ratio=30/1, vacuum port located near die face). The twin-screw extruder had enough distributive and dispersive mixing elements to produce good mixing of the polymer compositions. The compositions are subsequently molded according to ISO 294 on a Husky or BOY injection molding machine. Compositions were compounded and molded at a temperature of 250 to 330° C., though it will be recognized by one skilled in the art that the method is not limited to these temperatures.

The thermoplastic compositions are tested for the following properties. Yellowness Index (YI) for laboratory scale samples was determined using a HunterLab Color System at an illuminant observer of C/2°, in accordance with ASTM D1925-70 on 3.2±0.12 millimeter thick molded plaques. The color plaques were sealed in moisture-proof packaging prior to exposure to gamma radiation, and were kept from exposure to light. After exposure, the color plaques were measured for YI immediately after removal from the package and were not allowed to sit in the presence of fluorescent or UV light for any appreciable time period prior to taking the YI measurement. The increase in YI (dYI) is calculated by subtracting the yellowness index value of a non-irradiated sample (molded article) from that of an irradiated sample (molded article) of the same composition. Molecular weight was determined by gel permeation chromatography using a crosslinked styrene-divinyl benzene-packed column with an ultraviolet (UV) detector operating at 254 nm, and was calibrated against polycarbonate standards. The difference in weight averaged molecular weight is determined from a comparison of the weight averaged molecular weights of a sample and control.

Polycarbonate compositions for the examples and comparative examples were prepared using the components shown in Table 1.

TABLE 1

| | | |
|---|---|---|
| BPA-PC | BPA polycarbonate resin (MVR = 17.5 g/10 min at 300° C.) | GE Plastics |
| Bn-PC | Benzoate end-capped poly(bisphenol-A carbonate) | See Methods A, B, and C, below |
| MPD | 2-Methyl-2,4-pentanediol(hexylene glycol), 99% purity | Aldrich Chemical Co. |
| PETS | Pentaerythritol tetrastearate (mold release agent) | FACI Farasco, Genova, Italy |
| I-168 | IRGAFOS ® 168 (Tris(2,6-di-tert-butylphenyl)phosphite) (antioxidant) | Ciba Specialty Chemicals |
| ADR-4368 | JONCRYL ® ADR-4368 hydrolysis stabilizer | Johnson Polymer |

The polycarbonate resins and additives were blended in a powder mixer, extruded on a twin-screw extruder as described above, and injection molded into flat, rectangular plaques of 3.2±0.12 mm thickness, using the equipment described above. The aryl carboxylate end-capped polycarbonate, benzoate end-capped poly(bisphenol-A carbonate) (Bn-PC), was prepared using the method described below.

Benzoyl-capped Poly(Bisphenol-A Carbonate), Method A. The following were added into a 3 L, 5 necked Morton flask, equipped with an overhead condenser, an overhead stirrer, a pH probe, a caustic solution inlet, and a phosgene inlet: (a) 4,4-bis-(hydroxyphenyl)-2,2-propane (BPA) (25 g, 0.11 mol); (b) benzoyl chloride (Bn-Cl) (0.77 g, 0.006 mol); (c) triethylamine (0.23 mL, 0.002 mol); (d) methylene chloride (250 mL); and (e) de-ionized water (150 mL). The mixture was charged with phosgene (14.45 g, 2 g/min, 0.143 mol). During the addition of phosgene, base (50 wt % NaOH in deionized water) was simultaneously charged to the reactor to maintain the pH of the reaction between about 9 and about 11. After the complete addition of phosgene, the reaction was purged with nitrogen gas, and the organic layer was extracted for analysis by GPC.

Benzoyl-capped Poly(Bisphenol-A Carbonate), Method B. The following were added into a 3 L, 5 necked Morton flask, equipped with an overhead condenser, an overhead stirrer, a pH probe, a caustic solution inlet, and a phosgene inlet: (a) 4,4-bis-(hydroxyphenyl)-2,2-propane (BPA) (25 g, 0.11 mol); (b) benzoyl chloride (Bn-Cl) (0.77 g, 0.006 mol); (c) triethylamine (0.23 mL, 0.002 mol); (d) methylene chloride (250 mL); and (e) de-ionized water (150 mL). The reaction was allowed to stir for 10 minutes and the pH was maintained at about 8 to about 10 by the addition of 50% NaOH solution. The mixture was charged with phosgene (14.45 g, 2 g/min, 0.143 mol). During the addition of phosgene, base (50 wt % NaOH in deionized water) was simultaneously charged to the reactor to maintain the pH of the reaction between about 9 and about 11. After the complete addition of phosgene, the reaction was purged with nitrogen gas, and the organic layer was extracted for analysis by GPC.

Benzoate end-capped polycarbonate, Method C. The following were added into a 70 L CSTR equipped with an overhead condenser and a recirculation pump with a flow rate of 40 L/minute: (a) 4,4-bis-(hydroxyphenyl)-2,2-propane (BPA) (4540 g, 19.9 mol); (b) benzoyl chloride (113 g, 0.91 mol); (c) triethylamine (30 mL, 0.22 mol); (d) methylene chloride (16 L); (e) de-ionized water (14 L), and (f) sodium gluconate (10 g). The reaction was allowed to stir for 10 minutes and the pH was maintained at about 8 by the addition of 50% NaOH solution. The mixture was charged with phosgene (2688 g, 80 g/min, 29.6 mol). During the addition of phosgene, base (50 wt % NaOH in deionized water) was simultaneously charged to the reactor to maintain a pH of about 9 to about 11. After the complete addition of phosgene, the reaction was purged with nitrogen gas, and the organic layer was extracted. The organic extract was washed once with dilute hydrochloric acid (HCl), and subsequently washed with de-ionized water three times. The organic layer was precipitated from methylene chloride into hot steam. The polymer was dried in an oven at 110° C. before analysis. The Mw of the polycarbonate was measured to be 25,500 (referenced to polycarbonate standards) and polydispersity (Mw/Mn) is 3.6.

Molecular Weight Determination and Analysis of Residual Bn-Cl in Benzoate end-capped Poly(Bisphenol-A Carbonate). Benzoate end-capped polycarbonates prepared by Methods A (without pre-reaction of benzoyl chloride and bisphenol-A) and Method B (with pre-reaction of benzoyl chloride and bisphenol-A) were analyzed by gel permeation chromatography (GPC) according to the method described above. Each of Runs 1 and 2 were prepared identically using Method A, and likewise each of Runs 3 and 4 were prepared identically using Method B. The weight averaged molecular weight (Mw), polydispersity (Mw/Mn) and peak height corresponding to benzoyl chloride, as indexed to peak height of the polymer peak, are summarized in Table 2, below.

TABLE 2

| Benzoate end-capped PC Run no. | Bn-PC Method | Mw | Mw/Mn | Peak Height of Bn-Cl peak |
|---|---|---|---|---|
| 1 | A | 31,050 | 4.3 | 0.282 |
| 2 | A | 23,400 | 3.4 | 0.16 |
| 3 | B | 21,480 | 4.6 | 0.0286 |
| 4 | B | 22,730 | 4.7 | 0.0317 |

Note:
All Mw data determined using gel permeation chromatography (GPC).

As can be seen from the data in Table 2, benzoate end-capped poly(bisphenol-A carbonate)s prepared using Method B (Run Nos. 3 and 4) having a pre-reaction period included in the method, each exhibit a nearly complete benzoyl chloride conversion to the benzoate end-cap, as shown by the low, nearly undetectable peak heights corresponding to the residual benzoyl chloride as seen in the GPC-UV chromatogram, and the comparable Mw and polydispersities for these runs. In contrast, benzoate end-capped poly(bisphenol-A carbonate) prepared using Method A (without the pre-reaction period) exhibits up to 10 times higher residual benzoyl chloride level and hence a less complete reaction; a more variable and hence less well controlled Mw; and variable polydispersities. The pre-phosgenation reaction (in Method B) of the benzoyl chloride with BPA therefore provides a greater degree of conversion of the starting materials and control over the properties of the resulting benzoate end-capped polycarbonates prepared by this method. It was further noted during preparation of the benzoate end-capped polycarbonates that the pH control of the reaction, as evidenced by the amount of NaOH solution required to be added to maintain pH, and the variability in pH measurement, improved with pre-reaction of Bn-Cl and BPA. Slowing the phosgenation rate down slightly (by slowing the addition of phosgene) has also been found to favor the kinetics of benzoylation of BPA without the pre-reaction time, but did not improve the reaction kinetics or end-capping efficiency as much as pre-reaction of BPA and Bn-Cl prior to phosgenation.

Example 1 and Comparative Examples 1-3. Example 1 was prepared by combining BPA-PC, benzoate end-capped poly(bisphenol-A carbonate) (Bn-PC, prepared at larger scale according to Method C), at loadings of 10 or 20 wt % of the total weight of the BPA-PC and the Bn-PC, according to Table 2, below, and melt blending using the above-described processing conditions. Comparative Example 1 was prepared as described above using BPA-PC polycarbonate resin in place of the Bn-PC additive charge. In addition, in Comparative Examples 2 and 3, a hydrolysis stabilizer (ADR-4368) was included at a loading of 0.25 wt %. All examples and comparative examples contain 0.15 wt % MPD (aliphatic diol), 0.27 wt % PETS (plasticizer/mold release agent) and 0.027 wt % I-168 (antioxidant).

The pellets were injection molded into rectangular 3.2±0.12 mm thick plaques that were placed into a sealed package to prevent contact with light and moisture. The plaques were then subjected to high energy irradiation at nominal doses of 25, 50, or 75 kiloGrays (kGy) (common for sterilization; actual doses are reported in the tables), and subsequently measured for the change in yellowness index (dYI) according to the method described above which uses YI measurements according to ASTM D1925-70.

TABLE 2[1]

| | Bn-PC loading (wt %) | Hydr. Stab. Load (wt %) | dYI (30 kGy)[2] | dYI (59 kGy)[2] | dYI (81 kGy)[2] |
|---|---|---|---|---|---|
| Comparative Example 1 | 0 | 0 | 7.8 | 15.5 | 24.8 |
| Comparative Example 2 | 10 | 0.25 | 10.3 | 19.9 | 28.4 |
| Example 1 | 20 | 0 | 7.1 | 13.1 | 20.9 |
| Comparative Example 3 | 20 | 0.25 | 10.6 | 20.2 | 28.8 |

[1]All samples contain 0.15 wt % of MPD, 0.027 wt % of I-168, and 0.27 wt % of PETS.
[2]Irradiation doses reported in Table 3 in kiloGrays (kGy) are actual doses. A 25 kGy nominal dose gave a 30 kGy actual dose; a 50 kGy nominal dose gave a 59 kGy actual dose; and a 75 kGy nominal dose gave an 81 kGy actual dose.

Benzoyl-capped polycarbonate (Bn-PC), in which the benzoate end groups are separated by a medium molecular weight bisphenol-A polycarbonate, were examined for resistance to increased dYI. Polycarbonate compositions containing the Bn-PC in the absence of hydrolysis stabilizer (Example 1) exhibit decreased dYI compared to the Comparative Example 1, without Bn-PC. A sample having added hydrolysis stabilizer, seen in Comparative Example 2 (with 10 wt % Bn-PC), and Comparative Example 3 (with 20 wt % Bn-PC), yields less resistance to yellowing than either Example 1 (with Bn-PC), or Comparative Example 1 (without added Bn-PC or hydrolysis stabilizer). The inclusion of hydrolysis stabilizer, in this instance, has a substantially adverse effect on the dYI performance of the Bn-PC. Without wishing to be bound by theory, it is believed the epoxide moieties may be reacting with other high-energy species that are formed during the gamma ray irradiation of the polycarbonate compositions, and that these species interfere with the stabilization of the polycarbonate by any stabilizing species generated by irradiating the benzoate end groups.

Compounds are described herein using standard nomenclature. A dash ("-") that is not between two letters or symbols is used to indicate a point of attachment for a substituent. For example, —CHO is attached through the carbon of the carbonyl (C=O) group. The singular forms "a," "an," and "the" include plural referents unless the context clearly dictates otherwise. The endpoints of all ranges reciting the same characteristic or component are independently combinable and inclusive of the recited endpoint. All references are incorporated herein by reference. The terms "first," "second," and the like herein do not denote any order, quantity, or importance, but rather are used to distinguish one element from another. The notation "±0.012 mm" means that the indicated measurement can be from an amount that is 0.012 mm lower to an amount that is 0.012 mm higher than the stated value.

While typical embodiments have been set forth for the purpose of illustration, the foregoing descriptions should not be deemed to be a limitation on the scope herein. Accordingly, various modifications, adaptations, and alternatives may occur to one skilled in the art without departing from the spirit and scope herein.

I claim:

1. A thermoplastic composition comprising:
a polycarbonate that is not aryl carboxylate end-capped, and
an aryl carboxylate end-capped polycarbonate of formula:

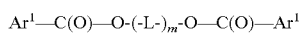

wherein each $Ar^1$ is independently an aryl group, $-(-L-)_m-$ is a polycarbonate linking group with m units of linking unit L, wherein L consists essentially of carbonate units wherein m is at least one, or a combination of carbonate units with poly(arylene ether) units, soft block units, or a combination comprising at least one of these, wherein m is 2 to 500 and at least one L is a carbonate unit;
wherein the aryl carboxylate end-capped polycarbonate has aryl carboxylate end groups present in the thermoplastic composition in an amount of 0.01 to 500 mmol/Kg based on the combined weights of the polycarbonate that is not aryl carboxylate end-capped, and the aryl carboxylate end-capped polycarbonate, and
wherein a molded article having a thickness of 3.2±0.12 millimeters and consisting of the aryl carboxylate end-capped polycarbonate, the polycarbonate that is not aryl carboxylate end-capped, and less than or equal to 1.0 percent total weight of aliphatic diol, a mold-release agent, and an antioxidant has, after exposure to a total gamma radiation dose of 81 kGy and when measured according to ASTM D1925-70, an increase in yellowness index (dYI) of less than or equal to 24.5, when compared to the unexposed molded article.

2. The thermoplastic composition of claim 1, wherein the aryl carboxylate end groups are present in the aryl carboxylate end-capped polycarbonate in amount of 0.01 to 10 mole-percent based on the total number of moles of linking unit L present in the aryl carboxylate end-capped polycarbonate.

3. The thermoplastic composition of claim 1, wherein the aryl carboxylate end-capped polycarbonate is present in an amount of 1 to 80 wt %, based on the total weight of the polycarbonate that is not aryl carboxylate end-capped, and aryl carboxylate end-capped polycarbonate, with the proviso that the amount and type of aryl carboxylate end-capped polycarbonate is selected so that the overall concentration of aryl carboxylate end groups is less than or equal to a molar concentration of 500 millimoles per kilogram (mmol/Kg), and is greater than or equal to 0.01 mmol/Kg, of the total weight of the polycarbonate that is not aryl carboxylate end-capped, and aryl carboxylate end-capped polycarbonate.

4. The thermoplastic composition of claim 1, wherein each $Ar^1$ is independently an unsubstituted $C_6$-$C_{20}$ aryl group, or substituted $C_6$-$C_{20}$ aryl group.

5. The thermoplastic composition of claim 1, wherein when-$(-L-)_m$- consist essentially of carbonate units, m is 1 to 500.

6. The thermoplastic composition of claim 1 wherein the poly(arylene ether) unit has the formula:

—(—$Ar^2$—X—$Ar^2$—O—)$_n$—$Ar^2$—X—$Ar^2$— wherein n is 0 to 200, wherein each $Ar^2$ is independently a substituted $C_6$-$C_{20}$ arylene group or unsubstituted $C_6$-$C_{20}$ arylene group; and wherein X is a bridging radical having one or two atoms that separate the $Ar^2$ groups.

7. The thermoplastic composition of claim 1, wherein soft block units consist essentially of polysiloxane units, polyalkylene oxide units, poly(alkylene ester) units, polyolefin units, or a combination comprising at least one of these.

8. The thermoplastic composition of claim 1, further comprising an ionizing radiation stabilizing additive.

9. The thermoplastic composition of claim 8, wherein the ionizing radiation stabilizing additive is an aliphatic alcohol, an aromatic alcohol, an aliphatic diol, an aliphatic polyol, an aliphatic ether, an ester, a diketone, an alkene, a thiol, thioethers, a cyclic thioether, a sulfone, a dihydroaromatic, a diether, a nitrogen compound, or a combination comprising at least one of the foregoing.

10. The thermoplastic composition of claim 9 wherein the aliphatic diol has the structure:

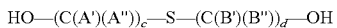
HO—(C(A')(A''))$_c$—S—(C(B')(B''))$_d$—OH wherein A', A'', B', and B'' are each individually H or $C_1$-$C_6$ alkyl; and wherein S is $C_1$-$C_{20}$ alkyl, $C_2$-$C_{20}$ alkyleneoxy, $C_3$-$C_6$ cycloalkyl, or $C_3$-$C_6$ substituted cycloalkyl; and wherein c and d are each 0 or 1, with the proviso that, where c and d are each 0, S is selected such that both —OH groups are not connected directly to a single common carbon atom.

11. The thermoplastic composition of claim 1, further comprising impact modifier, filler, antioxidant, heat stabilizer, light stabilizer, ultraviolet light absorber, plasticizer, mold release agent, lubricant, antistatic agent, pigment, dye, flame retardant, anti-drip agent, or a combination comprising at least one of these.

12. The thermoplastic composition according to claim 11 wherein the additive is selected such that it does not significantly adversely affect the dYI of the thermoplastic composition after treatment with an ionizing radiation.

13. The thermoplastic composition of claim 1, wherein the aryl carboxylate end-capped polycarbonate includes aryl carboxylate end-capped homopolycarbonate, aryl carboxylate end-capped copolycarbonate, aryl carboxylate end-capped polysiloxane-polycarbonate, aryl carboxylate end-capped polysiloxane-co-(polyester-polycarbonate), aryl carboxylate end-capped poly(arylene ether)-co-polycarbonate, aryl carboxylate end-capped poly(arylene ether)-co-(polyester-polycarbonate), aryl carboxylate end-capped poly(alkylene ester)-co-polycarbonate, aryl carboxylate end-capped poly(alkylene ester)-co-(polyester-polycarbonate), aryl carboxylate end-capped poly(alkylene ether)-co-polycarbonate, aryl carboxylate end-capped poly(alkylene ether)-co-(polyester-polycarbonate), aryl carboxylate end-capped polyolefin-co-polycarbonate, aryl carboxylate end-capped poly(olefin)-co-(polyester-polycarbonate), or a combination comprising at least one of these.

14. The thermoplastic composition of claim 1, wherein the aryl carboxylate end-capped polycarbonate is benzoate end-capped poly(bisphenol-A carbonate).

15. A thermoplastic composition comprising:
a polycarbonate that is not aryl carboxylate end-capped, and
an aryl carboxylate end-capped polycarbonate of formula:

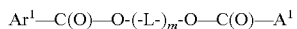
$Ar^1$—C(O)—O-(-L-)$_m$-O—C(O)—$A^1$ wherein each $Ar^1$ is independently an aryl group, $-(-L-)_m$- is a polycarbonate linking group with m units of linking unit L, wherein L consists essentially of carbonate units where m is at least oen, or a combination of carbonate units with poly(arylene ether) units, soft block units, or a combination comprising at least one of these wherein m is 2 to 500 and at least one L is a carbonate unit; and wherein the aryl carboxylate end-capped polycarbonate has aryl carboxylate end groups present in amount of 0.01 to 10 mole-percent based on the total number of moles of linking unit L present in the aryl carboxylate end-capped polycarbonate; and wherein the aryl carboxylate end-capped polycarbonate is present in an amount of 1 to 80 wt %, based on the total weight of the polycarbonate that is not aryl carboxylate end-capped, and aryl carboxylate end-capped polycarbonate, with the proviso that the amount and type of aryl carboxylate end-capped polycarbonate used is selected so that the overall concentration of aryl carboxylate end groups is less than or equal to a molar concentration of 500 millimoles per kilogram (mmol/Kg), and is greater than or equal to 0.01 mmol/Kg, of the total weight of the polycarbonate that is not aryl carboxylate end-capped, and aryl carboxylate end-capped polycarbonate.

16. A method of preparing an aryl carboxylate end-capped polycarbonate, comprising condensing:
a dihydroxy compound,
an aryl carboxylic acid halide, and
an activated carbonyl compound,
in a biphasic medium at a pH of about 9 to about 11, wherein the activated carbonyl compound is phosgene, diphosgene, triphosgene, a dichloroformate, or a combination comprising at least one of these, and wherein the aryl carboxylate end-capped polycarbonate has aryl carboxylate end groups present in an amount of 0.01 to 10 mole-percent based on the total number of moles of linking unit L present in the aryl carboxylate end-capped polycarbonate; and wherein the dihydroxy compound and aryl carboxylic acid halide are pre-condensed at a pH of 7.5 to 11, and for a time of 1 to 60 minutes, prior to condensing with the activated carbonyl compound.

17. The method of claim 16, wherein the dihydroxy compound comprises a dihydroxy aromatic compound, a dihydroxy poly(arylene ether), a dihydroxy soft-block compound, or a combination comprising at least one of these.

18. The method of claim 16, wherein the aryl carboxylic acid halide is present in the biphasic medium in an amount of less than or equal to 10 wt % of the initial charge of aryl carboxylic acid halide.

19. The method of claim 16 further comprising a phase transfer catalyst having the formula $(R)_4Q^{30}X$, wherein each R is the same or different, and is a $C_{1-10}$ alkyl group; Q is a nitrogen or phosphorus atom; and X is a halogen atom, a $C_{1-8}$ alkoxy group, or $C_{6-18}$ aryloxy group.

20. The method of claim 16, wherein the activated carbonyl compound is phosgene, wherein the dihydroxy compound is bisphenol-A, and wherein the aryl carboxylic acid halide is benzoyl chloride.

21. A method of making a thermoplastic composition comprising melt-blending:
a polycarbonate that is not aryl carboxylate end-capped, and
an aryl carboxylate end-capped polycarbonate of formula:

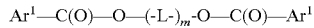

wherein each $Ar^1$ is independently an aryl group, $\text{-}(\text{-L-})_m\text{-}$ is a polycarbonate linking group with m units of linking unit L, wherein L consists essentially of carbonate units wherein m is at least one, or a combination of carbonate units with poly(arylene ether) units, soft block units, or a combination comprising at least one of these wherein m is 2 to 500 and at least one L is a carbonate unit;
wherein the aryl carboxylate end-capped polycarbonate has aryl carboxylate end groups present in amount of 0.01 to 10 mole-percent based on the total number of moles of linking unit L present in the aryl carboxylate end-capped polycarbonate, and
wherein the aryl carboxylate end-capped polycarbonate is present in an amount of 1 to 80 wt %, based on the total weight of the polycarbonate that is not aryl carboxylate end-capped, and aryl carboxylate end-capped polycarbonate, with the proviso that the amount and type of aryl carboxylate end-capped polycarbonate used is selected so that the overall concentration of aryl carboxylate end groups is less than or equal to a molar concentration of 500 millimoles per kilogram (mmol/Kg), and is greater than or equal to 0.01 mmol/Kg, of the total weight of the polycarbonate that is not aryl carboxylate end-capped, and aryl carboxylate end-capped polycarbonate.

22. An article comprising the thermoplastic composition of claim 1.

23. A sterilization method comprising exposing an article to radiation wherein the article comprises a polycarbonate that is not aryl carboxylate end-capped, and
an aryl carboxylate end-capped polycarbonate of formula:

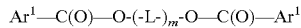

wherein each $Ar^1$ is independently an aryl group, $\text{-}(\text{L-})_m\text{-}$ is a polycarbonate linking group with m units of linking unit L, wherein L consists essentially of carbonate units wherein m is at least one, or a combination of carbonate units with poly(arylene ether) units, soft block units, or a combination comprising at least one of these wherein m is 2 to 500 and at least one L is a carbonate unit;
wherein the aryl carboxylate end-capped polycarbonate has aryl carboxylate end groups present in the thermoplastic composition in an amount of 0.01 to 500 mmol/Kg based on the combined weights of the polycarbonate that is not aryl carboxylate end-capped, and the aryl carboxylate end-capped polycarbonate.

24. The method according to claim 23 wherein a molded article having a thickness of 3.2±0.12 millimeters and consisting of the aryl carboxylate end-capped polycarbonate, the polycarbonate that is not aryl carboxylate end-capped, and less than or equal to 1.0 percent total weight of aliphatic diol, a mold-release agent, and an antioxidant has, after exposure to a total gamma radiation dose of 81 kGy and when measured according to ASTM D 1925-70, an increase in yellowness index (dYI) of less than or equal to 24.5, when compared to the unexposed molded article.

25. The method according to claim 23 wherein the aryl carboxylate end-capped polycarbonate is present in an amount of 1 to 80 wt %, based on the total weight of the polycarbonate that is not aryl carboxylate end-capped, and aryl carboxylate end-capped polycarbonate, with the proviso that the amount and type of aryl carboxylate end-capped polycarbonate used is selected so that the overall concentration of aryl carboxylate end groups is less than or equal to a molar concentration of 500 millimoles per kilogram (mmol/Kg), and is greater than or equal to 0.01 mmol/Kg, of the total weight of the polycarbonate that is not aryl carboxylate end-capped, and aryl carboxylate end-capped polycarbonate.

26. A thermoplastic composition comprising:
a polycarbonate that is not aryl carboxylate end-capped, and
an aryl carboxylate end-capped polycarbonate of formula:

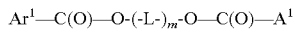

wherein each $Ar^1$ is independently an aryl group, $\text{-}(\text{-L-})_m\text{-}$ is a polycarbonate linking group with m units of linking unit L, wherein L consists essentially of carbonate units wherein m is at least one, or a combination of carbonate units with poly(arylene ether) units, soft block units, or a combination comprising at least one of these wherein m is 2 to 500 and at least one L is a carbonate unit, and m is at least one; and
an ionizing radiation stabilizing additive,
wherein the aryl carboxylate end-capped polycarbonate has aryl carboxylate end groups present in the thermoplastic composition in an amount of 0.01 to 500 mmol/Kg based on the combined weights of the polycarbonate that is not aryl carboxylate end-capped, and the aryl carboxylate end-capped polycarbonate, and
wherein a molded article having a thickness of 3.2±0.12 millimeters and consisting of the aryl carboxylate end-capped polycarbonate, the polycarbonate that is not aryl carboxylate end-capped, and less than or equal to 1.0 percent total weight of aliphatic diol, a mold-release agent, and an antioxidant has, after exposure to a total gamma radiation dose of 81 kGy and when measured according to ASTM D1925-70, an increase in yellowness index (dYI) of less than or equal to 24.5, when compared to the unexposed molded article.

* * * * *